(12) United States Patent
Watson et al.

(10) Patent No.: US 10,473,522 B2
(45) Date of Patent: *Nov. 12, 2019

(54) SPECTROMETER

(71) Applicant: MKS TECHNOLOGY, Centennial, WY (US)

(72) Inventors: Mark Watson, Laramie, WY (US); Shane Buller, Laramie, WY (US); Keith Carron, Centennial, WY (US)

(73) Assignee: MKS TECHNOLOGY, Centennial, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/727,415

(22) Filed: Oct. 6, 2017

(65) Prior Publication Data

US 2018/0283941 A1 Oct. 4, 2018

Related U.S. Application Data

(63) Continuation of application No. 13/907,812, filed on May 31, 2013, now Pat. No. 9,791,313, which is a continuation-in-part of application No. 13/221,899, filed on Aug. 31, 2011, now Pat. No. 8,988,678.

(60) Provisional application No. 61/418,540, filed on Dec. 1, 2010, provisional application No. 61/450,123, filed on Mar. 7, 2011.

(51) Int. Cl.
*G01J 3/02* (2006.01)
*G01J 3/06* (2006.01)
*G01J 3/44* (2006.01)
*G01N 21/65* (2006.01)

(52) U.S. Cl.
CPC ............... *G01J 3/0208* (2013.01); *G01J 3/06* (2013.01); *G01J 3/44* (2013.01); *G01N 21/65* (2013.01); *G01J 2003/062* (2013.01); *G01J 2003/064* (2013.01)

(58) Field of Classification Search
CPC ...................................................... G01J 3/0208
USPC .......................................................... 356/326
See application file for complete search history.

(56) References Cited

U.S. PATENT DOCUMENTS

| | | |
|---|---|---|
| 5,646,411 A | 7/1997 | Kain et al. |
| 5,719,391 A | 2/1998 | Kain |
| 6,172,785 B1 | 1/2001 | Wulf |
| 6,384,951 B1 | 5/2002 | Basiji |

(Continued)

FOREIGN PATENT DOCUMENTS

JP 2002 372456 12/2002

OTHER PUBLICATIONS

Horiba Scientific Technical Note, "Dual Scan (TM) Imaging, Raman RA-TN04", Jan. 2012 Copyright notice, Jobin Yvon Technology, 4 pages.

(Continued)

*Primary Examiner* — Kara E. Geisel
*Assistant Examiner* — Omar H Nixon
(74) *Attorney, Agent, or Firm* — FisherBroyles, LLP; Thomas J. Osborne, Jr.

(57) ABSTRACT

A spectrometer is provided. In one implementation, for example, a spectrometer comprises an excitation source, a focusing lens, a movable mirror, and an actuator assembly. The focusing lens is adapted to focus an incident beam from the excitation source. The actuator assembly is adapted to control the movable mirror to move a focused incident beam across a surface of the sample.

17 Claims, 18 Drawing Sheets

(56) References Cited

U.S. PATENT DOCUMENTS

| | | | |
|---|---|---|---|
| 6,882,477 B1 | 4/2005 | Schattenburg et al. | |
| 6,950,185 B1 * | 9/2005 | Da Silva | G01J 3/2823 356/326 |
| 7,403,281 B2 | 7/2008 | Carron et al. | |
| 7,570,367 B2 | 8/2009 | Ohashi et al. | |
| 7,595,873 B1 | 9/2009 | Deck | |
| 8,125,637 B2 | 2/2012 | Carron et al. | |
| 2006/0285109 A1 | 12/2006 | Odhner | |
| 2007/0091409 A1 | 4/2007 | Ulbricht | |
| 2007/0285659 A1 * | 12/2007 | Hsieh | G01J 3/02 356/308 |
| 2009/0262359 A1 | 10/2009 | Bajraszewski et al. | |
| 2009/0316150 A1 * | 12/2009 | Myrick | G01J 3/02 356/326 |
| 2012/0162642 A1 | 6/2012 | Watson et al. | |

OTHER PUBLICATIONS

ISA/US International Search Report dated Feb. 17, 2015 in reference to co-pending International Application No. PCT/IB2014/001434 filed Jul. 31, 2014.

International Bureau of WIPO International Preliminary Report on Patentability dated Dec. 1, 2015 in reference to co-pending International Application No. PCT/IB2014/001434 filed Jul. 31, 2014.

Naoki Matsumoto et al: "Development of THz Ellipsometer with Variable Incident angle", NFRARED, Millimeter, and Terahertz Waves, 2009. IRMMWTHZ 2009. 34th International Conference on, IEEE, Piscataway, NJ, USA, Sep. 21, 2009 (Sep. 21, 2009 ), pp. 1-2.

Search Report for EP Application No. 14804678.2-1554 dated May 12, 2017, 17 pages.

\* cited by examiner

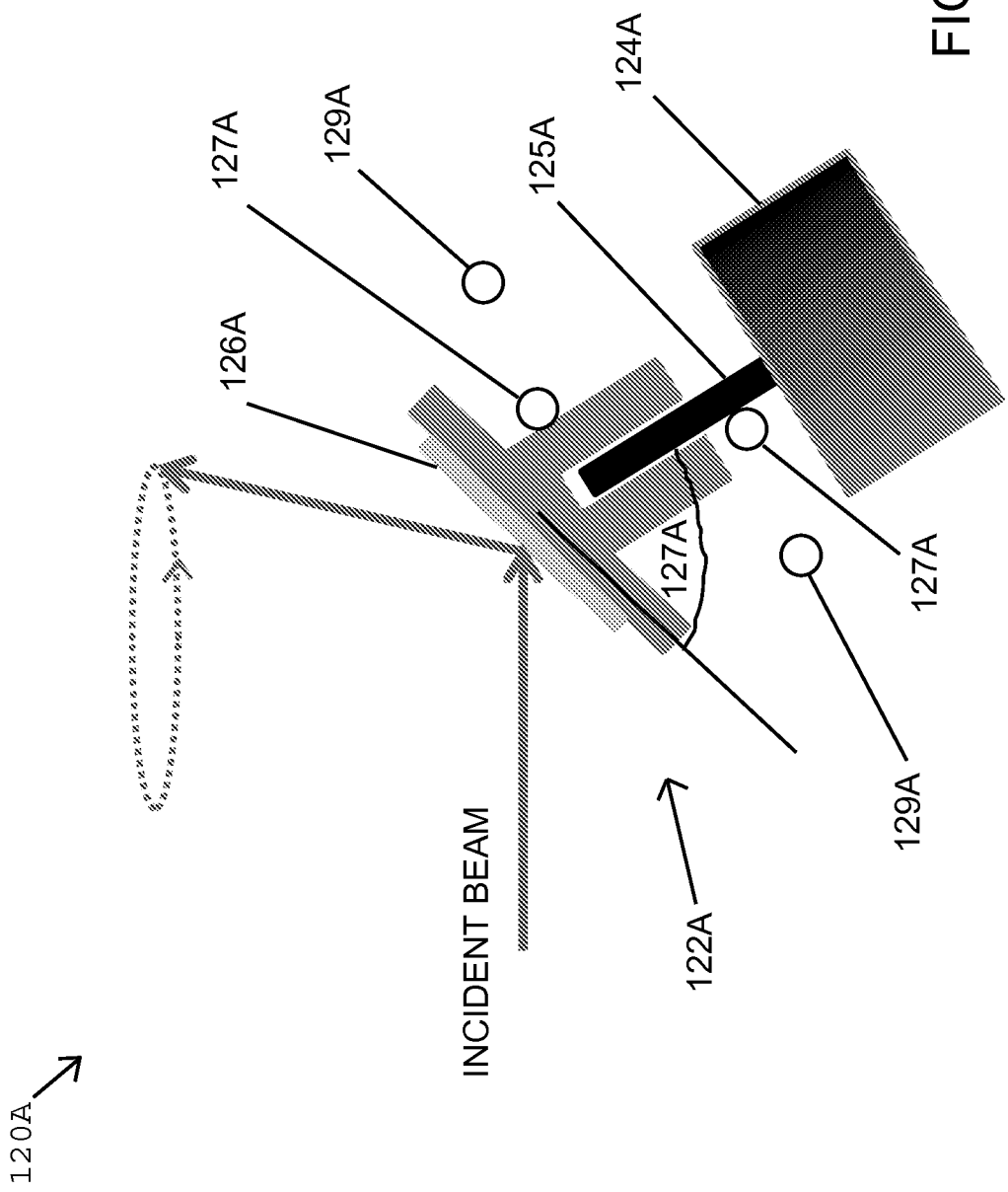

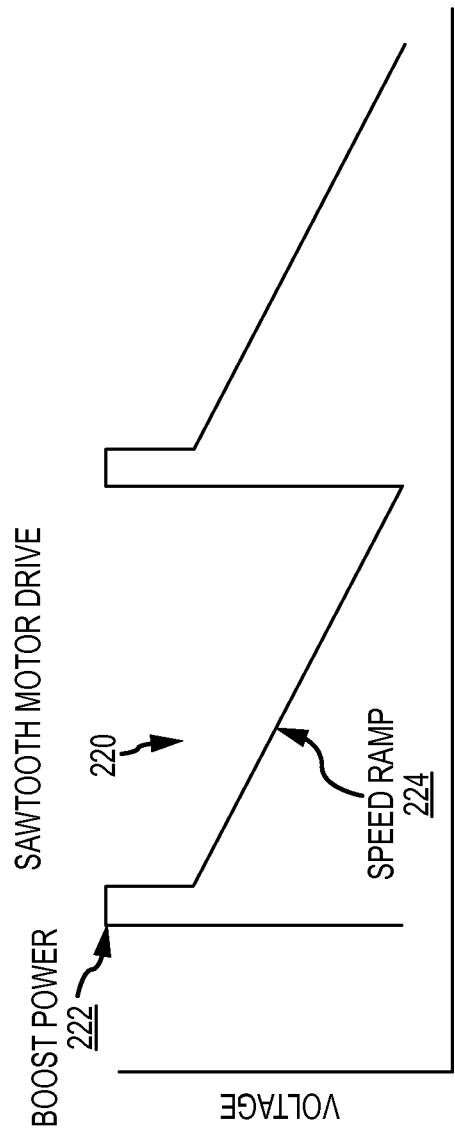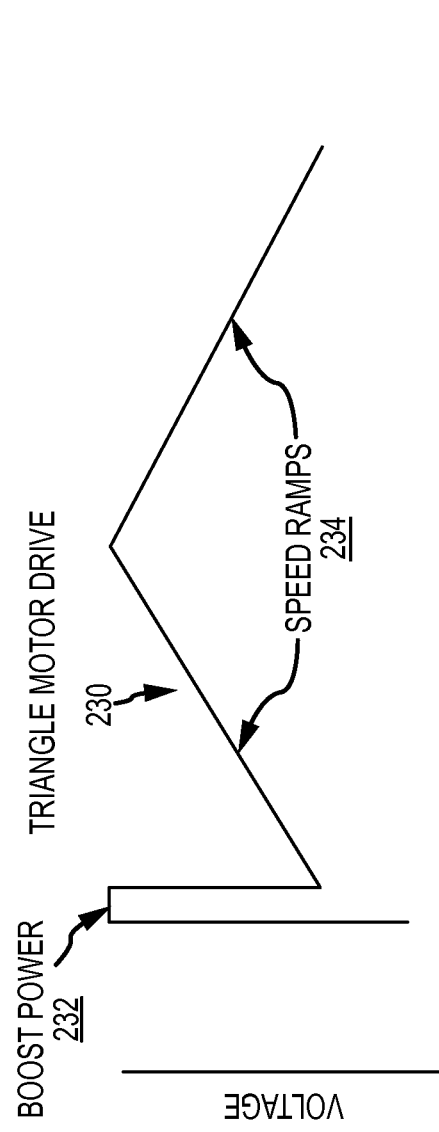

SPECTROMETER

CROSS-REFERENCE TO RELATED APPLICATIONS

This application is a continuation of U.S. patent application Ser. No. 13/907,812 entitled "Spectrometer" and filed by Mark Watson et al. on May 31, 2013, which is a continuation-in-part of U. S. patent application Ser. No. 13/221,899entitled "Spectrometer" and filed by Mark Watson et al. on Aug. 31, 2011, All the foregoing applications are hereby incorporated by reference in its entirety as if fully set forth herein and by applicable United States law.

This application also claims the benefit of U.S. provisional patent application No. 61/378,383 filed on Aug. 30, 2010 filed by Carron; U.S. provisional patent application No. 61/418,540 filed on Dec. 1, 2010 by Carron; and U.S. provisional patent application No. 61/450,123 filed on Mar. 7, 2011 by Carron et al. Each of the provisional applications are hereby incorporated by reference in their entirety as though fully set forth herein.

BACKGROUND OF THE INVENTION a. Field of the Invention

The instant invention relates to a spectrometer. In particular, the instant invention relates to a spectrometer configured to move a focused incident beam across a sample.

b. Background

A spectrometer (e.g., a Raman or luminescence (e.g., fluorescence, phosphorescence, chemiluminescence) spectrometer) is provided that provides a relatively large spectral area while maintaining a reasonable spectral resolution. Although particular types of spectrometers are described below (e.g., Raman and fluorescent), these are merely examples of spectrometers that may be used in a similar manner to move a focused beam across a sample to provide a larger sampling area while maintaining spectral resolution of the spectrometer

BRIEF SUMMARY OF THE INVENTION

In one implementation, a spectrometer is provided comprising an excitation source for providing an excitation signal, a detector for detecting a spectroscopy signal and an optical system for directing an incident beam of the excitation signal toward a sample, receiving the spectroscopy signal from the sample, and providing the spectroscopy signal to the detector. The optical system comprises: a focusing lens for focusing the incident beam from the excitation source; a rotating mirror assembly including an angled mirror face surface; and an actuator assembly for controlling the rotating mirror assembly to move a focused incident beam across a surface of the sample, wherein the actuator assembly comprises a rotary motor coupled to the rotating mirror assembly and adapted to rotate the angled mirror face to redirect an incident beam of the excitation signal.

In another implementation, a method of moving a focused incident beam of a spectrometer across a surface of a spectroscopic sample is provided. In this implementation, the method comprises: generating an incident beam of an excitation signal; directing the incident beam towards the sample via an optical system of the spectrometer, the optical system comprising a moveable mirror; focusing the incident beam on a sample of the spectrometer; moving the incident beam across a surface of the sample by rotating a rotating mirror assembly coupled to a drive shaft of a rotary motor by rotating the drive shaft; receiving a spectroscopic signal from the sample; and detecting the spectroscopic signal.

In one implementation, a spectrometer comprising a magnetic positioning system is provided. In this implementation, the spectrometer comprises: an excitation source for providing an excitation signal; a detector for detecting a spectroscopy signal; an optical system for directing an incident beam of the excitation signal toward a sample, receiving the spectroscopy signal from the sample, and providing the spectroscopy signal to the detector and a magnetic positioning system. The optical system comprises: a focusing lens for focusing the incident beam from the excitation source; a moveable mirror; and an actuator assembly for controlling the moveable mirror to move a focused incident beam across a surface of the sample. The magnetic positioning system comprises a magnet and a second element adapted to magnetically couple to the magnet. The magnetic positioning system is configured to position the moveable mirror in a predetermined position by magnetically coupling at least one magnet to a second element. One of the magnet and the second element is physically coupled to the actuator assembly and the other one of the magnet and the second element is fixed to the spectrometer adjacent to the actuator assembly.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 7A and 7B show other example implementations of actuator assemblies for moving an incident beam across a surface of a sample.

FIGS. 11 and 12 show waveforms of example motor drive waveforms that may be used to control the motors of the implementations shown in FIGS. 2-5 and 10.

DETAILED DESCRIPTION

A spectrometer (e.g., a Raman or luminescence (e.g., fluorescence, phosphorescence, chemiluminescence) spectrometer) is provided that provides a relatively large spectral area while maintaining a reasonable spectral resolution. Although particular types of spectrometers are described below (e.g., Raman and fluorescent), these are merely examples of spectrometers that may be used in a similar manner to move a focused beam across a sample to provide a larger sampling area while maintaining spectral resolution of the spectrometer.

In one implementation, for example, a relatively low-cost, handheld Raman (or other) spectrometer is provided that provides rapid authentication (e.g., a point-and-shoot method requiring <10 sec) of SERS-active targets (e.g., fibers). The spectrometer, for example, can use a programmable, on-board taggant matching capability. In various implementations, this instrument can be used for contact detection and/or standoff detection of SERS-active materials (e.g., textile substrates from a distance of, for example, 0-2 meters).

In another implementation, a fluorescence (or other) spectrometer rasters (or otherwise moves) a focused beam across a surface of a tagged target. In one variation, for example, the spectrometer averages the signals received from the sample. As described in the attached appendix, the averaged signals received from an excitation beam rastered across a sample can be used to detect a concentration of a tag or other detectable element dispersed within a heterogeneous sample. Thus, if a concentration of a sample (e.g., a tagged paint) is known, an averaged spectrometer signal can be used to detect if the sample has been diluted from the known concentration.

Figure 1:
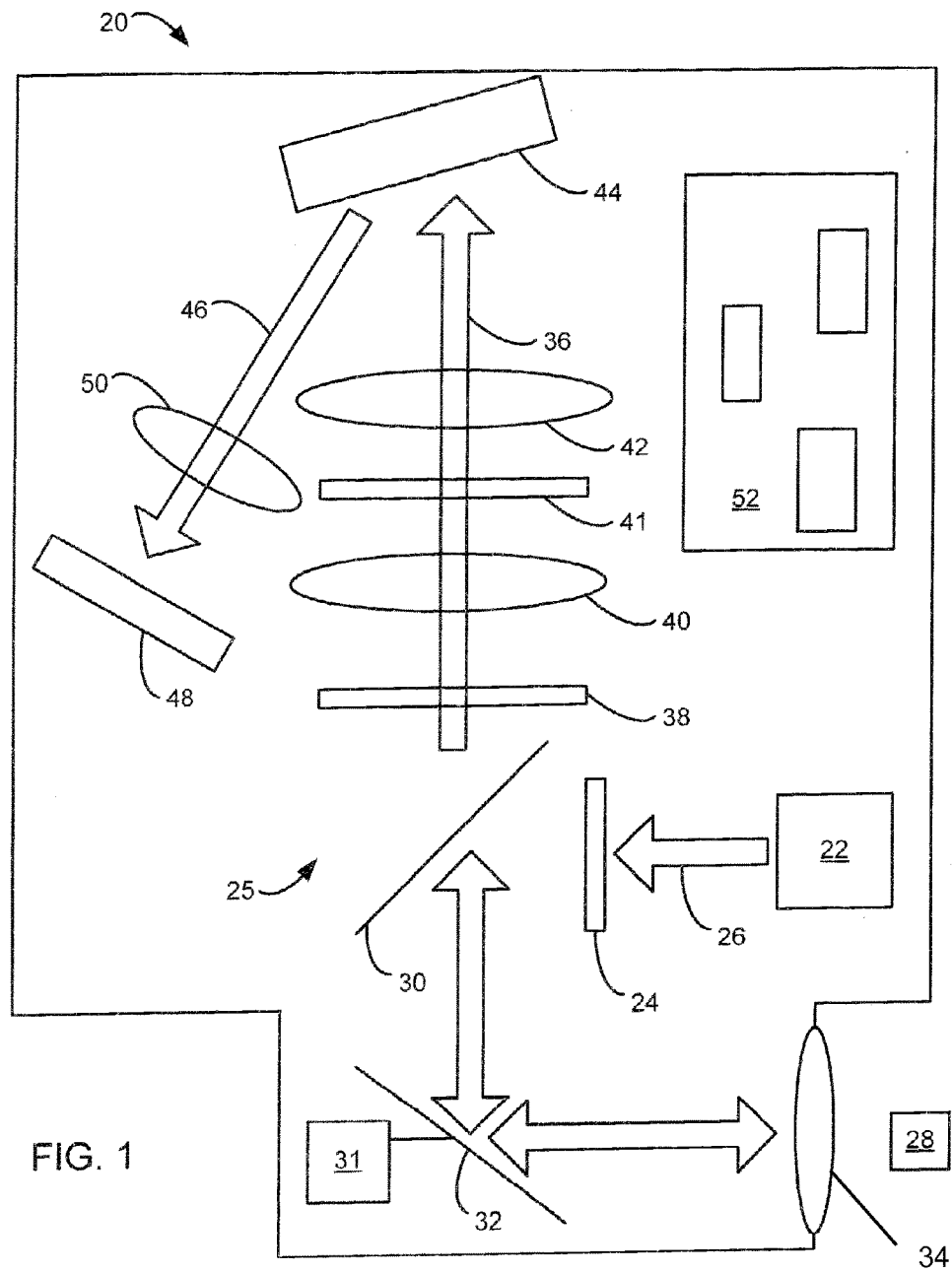
FIG. 1 shows an example embodiment of a spectrometer configured to move a focused beam across a surface of a target.

FIG. 1 shows an example embodiment of a spectrometer 20 configured to move a focused beam across a surface of a target. Although the particular example shows a Raman spectrometer, other types of spectrometers, such as a luminescence spectrometer, could readily be designed based on the description herein. As shown in FIG. 1, the spectrometer 20 comprises an excitation source 22. In a Raman spectrometer, for example, the excitation source 22 typically comprises a laser light source. In one embodiment, for example, the excitation source 22 comprises a diode laser. A diode laser, for example, is capable of providing a plurality of wavelengths from the excitation source 22. The spectrometer 20 further comprises a filter 24. The filter 24 filters the output of the excitation source 22, such as removing spurious emissions from the excitation source 22.

The spectrometer 20 further comprises an optical system 25. The optical system 25 directs the incident beam 26 toward a sample 28 and receives a spectroscopy signal from the sample 28. In the embodiment shown in FIG. 1, for example, the optical system 25 comprises a dichroic beam-splitter mirror 30. However, the incident beam 26 may be directed at sample 28 without any intervening instrument components located in the path of incident beam 26. The incident beam 26 also may be directed at a mirror, a holographic transmissive element, a mirror formed with a hole in the mirror or any other means for directing an incident beam known in the art.

The optical system 25 further comprises a means for moving the incident beam across a surface of the sample 28. In one embodiment, for example, an actuator assembly 31 moves (e.g., vibrates) one or more element of the optical system 25 (e.g., a moveable mirror 32) to move a focused beam across a surface of the sample 28. The actuator assembly 31, for example, may control the moveable mirror 32 to move a focused incident beam 26 across a surface of the sample 28. The actuator assembly 31, for example, may control the moveable mirror 32 to move the incident beam in any path or pattern across the surface of the sample 28. In one implementation, for example, the actuator assembly 31 may control the moveable mirror 32 in such a manner as to trace one or more line, circle, elliptical or other paths across the surface of the sample. FIGS. 2 through 10, described below, describe a number of example actuator assemblies 31 for use in the spectrometer 20.

The incident beam 26 may further be directed through a lens 34. In one embodiment, the lens 34 comprises a focusing lens in the path of the incident beam 26. The focusing lens couples the incident beam 26 with the sample 28 and collects the spectroscopy signal (e.g., Raman scattered light) from the sample. In another embodiment, more than one lens 34 may be located in the path of the incident beam 26 before the incident beam 26 contacts the sample 28. In various embodiments, the spectrometer 20 may include other optical elements for directing an incident beam 26 toward a sample and collecting a spectroscopy signal from the sample. The optical system of the spectrometer 20, for example, may include elements such as a collimated beam tube or a fiber optic waveguide. See, e.g., U.S. Pat. No. 7,403,281 for examples of collimated beam tubes or fiber optic waveguides that may be used in optical systems of various spectrometers.

The incident beam 26 induces or generates on contact with the sample 28 a spectroscopy signal to be detected by the spectrometer 20. In Raman spectroscopy, for example, the incident beam 26 induces or generates on contact with the sample 28 scattered radiation having an energy differential different from, and one or more wavelengths different than, the incident radiation 26, or the Raman shift that, for convenience, is described in this document as a Raman beam. As stated above, and as shown in FIG. 1, in one embodiment the spectrometer 20 comprises a beam-splitter, such as a dichroic beam-splitter mirror 30. The spectroscopy signal 36 (e.g., Raman beam) is directed back through the lens 34 and the dichroic beam-splitter mirror 30 in a 180 degree back-scatter geometry. Neither the incident beam 26 nor the spectroscopy signal 36 need be co-linear. In the embodiment shown in FIG. 1, however, the spectroscopy signal 36 passes back through the dichroic beam-splitter mirror 30 and then through a filter element 38. In one embodiment, the filter element 38 comprises a long pass filter that removes extraneous radiation (e.g., from the light source 22 or another source) prior to dispersing the spectroscopy signal 36 into a spectrum. Alternatively, the filter element 38 may comprise a notch filter, or any other filter that is capable of rejecting elastically scattered radiation.

The spectroscopy signal 36 may further pass through an input focusing lens 40 that focuses the spectroscopy signal 36 to a point at a spatial filter 41. In one embodiment, for example, the spatial filter 41 comprises an aperture, slit or notch and is located at the focal point of the input focusing lens 40. The spatial filter 41 spatially filters the beam at the focal point of the input focusing lens.

The spectrometer 20 shown in FIG. 1 further comprises a collimating lens 42 that collimates the diverging spectroscopy signal 36 after it has passed through an aperture of the spatial filter 41 (e.g., an aperture, slit or notch). The collimating lens 42 further directs the re-collimated Raman beam toward a diffraction grating 44. The diffraction grating 44 comprises an optical element that divides a Raman beam into spatial separated wavelengths. The diffraction grating 44 further directs a divided Raman beam 46 toward a detector 48. The divided Raman beam 46 passes through a detector focusing lens 50 that focuses the spatially separated wavelengths of the divided Raman beam 46 onto the detector 48.

The detector 48 comprises a transducer that converts optical energy into an electrical signal. In one embodiment, for example, the detector 48 comprises an array of individual transducers that create an electrical pattern representing the spatially separated wavelengths of the Raman spectrum. A charge-coupled device (CCD) array, for example, may be used as the detector 48 in one embodiment of the invention. In another embodiment, an Indium-Gallium-Arsenide (In-GaAs) detector 48. Other detectors known in the art may also be used within a spectrometer of the present invention.

The spectrometer 20 further comprises control electronics 52 for controlling the operation of the spectrometer 20. The control electronics 52, for example, may control the operation of the light source 22, the actuator assembly 31, the detector 48, temperature control elements (e.g., for the light source or detector), and data transfer to and/or from the spectrometer. In one embodiment, the control electronics 52 may be integrated onto a single PC board within a housing of the spectrometer. The control electronics 52 may also comprise one or more discrete component(s) and/or one or more integrated circuit component(s).

In one embodiment, the control electronics 52 may comprise a means for communicating with an external device. The means for communicating, for example, the means form communicating may comprise a wired or wireless communication port for communicating with an external computer, personal data assistant (PDA), network or the like. A wired communication port, for example, may comprise a parallel, serial, universal serial bus (USB), FireWire™, IEEE 1394, Ethernet, modem, cable modem or other wired communication port known in the art. A wireless communication port, for example, may comprise an antenna for wireless communicating with an external device, such as via and infrared, Bluetooth, IEEE 802.11a/b/g, IrDA, a wireless modem or other wireless communication port known in the art. The control electronics 52 may be powered from a battery for a portable device or may include a power input for receiving power from an external supply as known in the art. A battery or power supply circuit (e.g., a rectifier) may be located within a housing of the spectrometer 20.

In Raman spectroscopy, the spectrometer 20 operates to detect a Raman spectrum of a sample 28. In order to detect the Raman spectrum, the light source 22 is activated to generate an incident beam 26 of excitation radiation, such as generating a laser incident beam in a laser light source. In one embodiment, for example, the temperature of the light source 22 is controlled to control the output frequency of the incident beam 26 generated by the light source 22. The incident beam 26 of excitation radiation passes through the filter 24, which removes spurious emissions from the incident beam. The incident beam 26 is reflected off the beam-splitter mirror 30 toward the sample 28. The incident beam 26 is focused onto the sample 28 by the output focusing lens 34.

The incident beam 26 generates Raman scattered light from the sample 28. The Raman scattered light is received by the output focusing lens 34 and transmitted back through the beam-splitter mirror 30. In this embodiment, the beam-splitter mirror 30 passes the Raman scattered light through the mirror 30 to the filter 38. From the filter 38, the Raman scattered light passes through the input focusing lens 40 and is focused onto a spatial filter 41 such as an aperture, slit or notch. The Raman scattered light is spatially filtered and diverges toward the collimating lens 42. The collimating lens 42 collimates the diverging Raman scattered light and transmits the light to the diffraction grating 44, which divides the Raman scattered light into spatial separated wavelengths and directs the wavelengths towards the detector element 48. The spatially separated wavelengths of the Raman scattered light pass through the detector focusing lens 50 and are focused into a focused band of radiation that represents the spatially separated wavelengths of the Raman scattered light. The focused band of radiation is further directed by the detector focusing lens 50 onto the detector 48.

In this particular implementation, the detector 48 comprises an array of individual transducers that each generate an electrical signal corresponding to intensity of the radiation received at each of the individual transducers. The electrical signals generated at the individual transducers of the detector represents the spatially separated wavelengths of the Raman spectrum of the sample 28. The electrical signals are read from the detector by the control electronics 52. In one embodiment, for example, the spectrometer 20 may then present the Raman spectrum detected to a user such as via a display or indicator on the spectrometer itself. In another embodiment, the control electronics of the spectrometer 20 may comprise a look-up table stored in a data storage element (e.g., memory, tape or disk drive, memory stick or the like). In this embodiment, the control electronics 52 compares the signal from the detector with the values stored in the look-up table to determine a result of the Raman scan. The spectrometer 20 then presents the result to a user such as via a display or indicator on the spectrometer. The result, for example, may indicate the presence or absence of one or more chemicals or substances in the sample and may further indicate an amount or concentration of a chemical or substance detected by the spectrometer.

In other implementations, the detector 48 may comprise one or more individual transducers that rapidly scan for one or more anticipated spectral features (e.g., Raman features). An example such system is disclosed in U.S. patent application Ser. No. 13/161,485 entitled "Spectrometer" and filed by Carron et al. on Jun. 15, 2011, which is hereby incorporated herein by reference in its entirety for all that it teaches and suggests.

Figure 2:
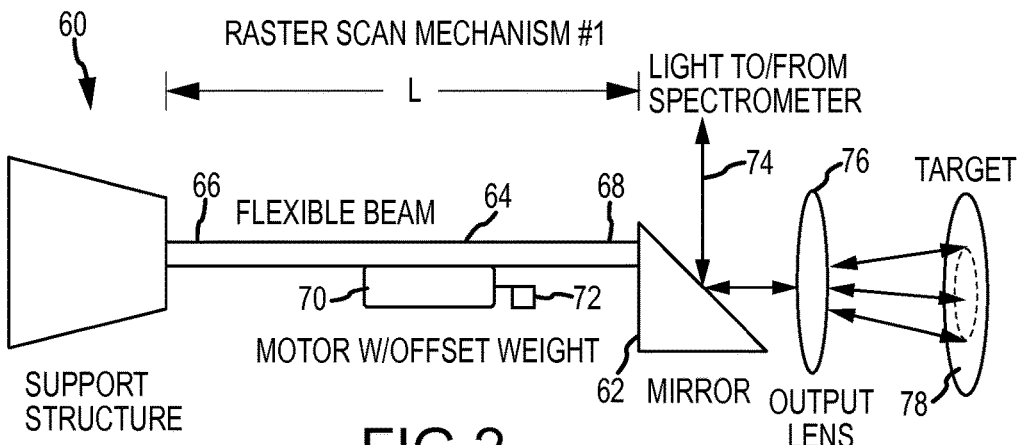
FIG. 2 shows an example implementation of an actuator assembly for moving an incident beam of a spectrometer across a surface of a sample.

FIG. 2 shows an example implementation of an actuator assembly 60 for moving an incident beam of a spectrometer across a surface of a sample. The actuator assembly 60, for example, may move one or more elements of an optical system of the spectrometer to scan, raster or otherwise move the incident beam across the surface of the sample.

In the particular implementation shown in FIG. 2, a mirror 62 (or other optical element) is coupled to a flexible beam 64. The mirror 62 may, for example, correspond to the moveable mirror 32 shown in FIG. 1. A first proximal end 66 of the flexible beam 64 is anchored and a second distal end 68 of the flexible beam 64 is coupled to the mirror 62. Although the flexible beam is shown anchored at the first proximal end 66 and coupled to the mirror 62 at the second distal end 68, the flexible beam 64 may be anchored and/or coupled to the mirror 62 at any point along a length L of the flexible beam 64. As the beam 64 flexes (e.g., due to force bending and/or torsion), the mirror 62 is moved with respect to one or more other optical element, such as a focusing lens, of the spectrometer. The movement of the beam 64, for example, may alter an angle of the mirror 62 and redirect the incident beam from a static path. A collimated incident beam hits the mirror 62 and then is focused through a stationary output lens 76 onto a spot of the sample 78. The size and shape of an area being illuminated can be changed with motor speed, beam shape, beam stiffness, and the like. In addition, a speed of the motor 70 can be changed (e.g., ramped) in a fashion to maximize the illuminated area.

The flexible beam 64 may comprise any relatively flexible material. In one implementation, for example, the flexible beam may comprise a 1/8" or 3/32" tube of polystyrene. Other relatively high modulus materials (e.g., brass or a helical steel spring) that are able to vibrate without unduly absorbing energy may also be used.

The flexible beam 64 may be moved by any number of actuators. In the particular implementation shown in FIG. 2, for example, a motor 70 comprising an offset weight 72 (e.g., a cell phone vibrator motor) is coupled to the flexible beam 64 offset from the anchor point of the flexible beam (e.g., the first proximal end 66). As the motor 70 is excited, the offset weight 72 vibrates the flexible beam 64, moving the optical element coupled to the flexible beam 64. In this implementation, the optical element comprises the moveable mirror 62 that reflects an incident excitation beam 74 from the spectrometer towards an output focusing lens 76 that focuses the incident beam onto the sample 78. By moving the mirror 62, the actuator assembly 60 moves the incident beam 74 across a surface of the sample 78. A spectroscopy signal induced at the sample by the incident beam 76 is received via the output focusing lens 76, reflected back off the moveable mirror 74 and passed through a dichroic beam-splitter mirror of the spectrometer (see, e.g., beam-splitter mirror 30 in FIG. 1).

The movement of the one or more optical elements coupled to the flexible beam 64 can be controlled by applying one or more control signals to the motor 70. FIGS. 11 and 12, described below, show example control waveforms that can be used to control the motion of one or more of the optical element(s) (such as the mirror 62) and, in turn, the motion of the incident beam 74 across the surface of the sample 78.

The actuator assembly 60 may be used to move the incident beam 74 across the surface of the sample 78 in any number of patterns or paths. The actuator assembly 60, for example, may move the mirror 62 in a line, ellipse, circle or other controlled or uncontrolled manner to move the incident beam across the surface of the sample in any number of patterns or paths. The movement of the incident beam 74 across the surface of the sample 78 thus allows the spectrometer to sample a larger area of the sample without reducing the resolution of the spectrometer.

Figure 3:
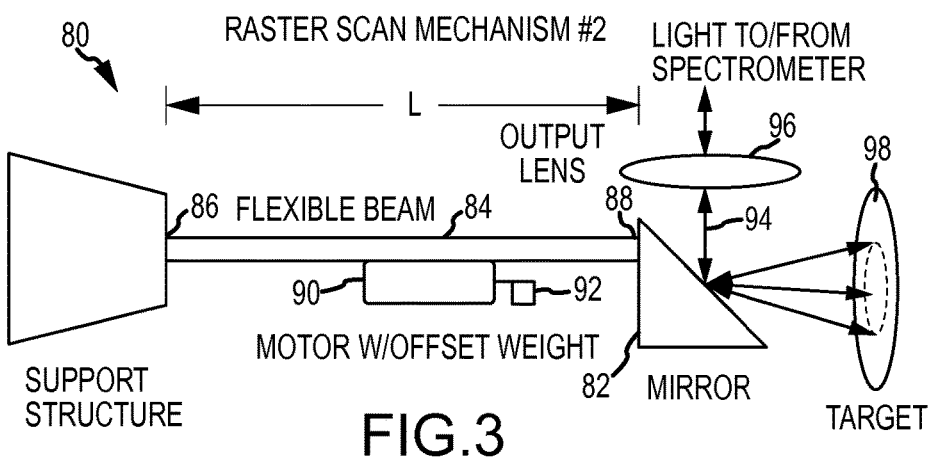
FIG. 3 shows another example implementation of an actuator assembly for moving an incident beam of a spectrometer across a surface of a sample.

FIG. 3 shows another example implementation of an actuator assembly 80 for moving an incident beam of a spectrometer across a surface of a sample. Similar to the actuator assembly 60 shown in FIG. 2, the actuator assembly 80 shown in FIG. 3 moves one or more optical elements of a spectrometer to scan, raster or otherwise move the incident beam across the surface of the sample.

In the particular implementation shown in FIG. 3, a mirror 82 (or other optical element) is coupled to a flexible beam 84, such as described above with respect to FIG. 2. As in FIG. 2, the mirror 82 may correspond to the moveable mirror 32 shown in FIG. 1. A first proximal end 86 of the flexible beam 84 is anchored and a second distal end 88 of the flexible beam 84 is coupled to the mirror 82. Again, although the flexible beam 84 is shown anchored at the first proximal end 86 and coupled to the mirror 82 at the second distal end 88, the flexible beam 84 may be anchored and/or coupled to the mirror 82 at any point along a length L of the flexible beam 84. As the beam 84 flexes (e.g., due to force bending and/or torsion), the mirror 82 is moved with respect to one or more other optical element, such as a focusing lens 96, of the spectrometer. The movement of the beam 84, for example, may alter an angle of the mirror 82 and redirect the incident beam from a static path. A converging incident beam (received via the focusing lens 96) hits the mirror 82 and is redirected to form a focused spot or area on the sample 98. As described above with respect to FIG. 2, the size and shape of an area being illuminated on the sample 98 can be changed with motor speed, beam shape, beam stiffness, and the like. In addition, a speed of the motor 90 can be changed (e.g., ramped) in a fashion to maximize the illuminated area.

The flexible beam 84 may be moved by any number of actuators. In the particular implementation shown in FIG. 3, for example, a motor 90 comprising an offset weight 92 (e.g., a cell phone vibrator motor) is coupled to the flexible beam 84 offset from the anchor point of the flexible beam 84 (e.g., the first proximal end 86). As the motor is excited, the offset weight 92 vibrates the flexible beam 84, moving the optical element coupled to the flexible beam 84. In this implementation, the optical element comprises the mirror 82 that reflects an incident excitation beam 94 from an output lens 96 of the spectrometer towards a sample 98. By moving the mirror 82, the actuator assembly 80 moves the incident beam 94 across a surface of the sample. A spectroscopy signal induced at the sample by the incident beam 94 is received via the mirror 82 and either reflected to the output lens 96 of the spectrometer or passed through the mirror (e.g., for a dichroic beam-splitter mirror or a mirror with an aperture for receiving spectroscopy signals).

As described above with respect to FIG. 2, the movement of the one or more optical elements coupled to the flexible beam 84 can be controlled by applying one or more control signals to the motor 90. FIGS. 11 and 12, described below, show example control waveforms that can be used to control the motion of the optical element(s) and, in turn, the motion of the incident beam 94 across the surface of the sample 98.

The actuator assembly 80 may be used to move the incident beam across the surface of the sample 98 in any number of patterns or paths. The actuator assembly 80, for example, may move the mirror 82 in a line, ellipse, circle or other controlled or uncontrolled manner to move the incident beam across the surface of the sample in any number of patterns or paths. The movement of the incident beam across the surface of the sample thus allows the spectrometer to sample a larger area of the sample 98 without reducing the resolution of the spectrometer.

Figure 4:
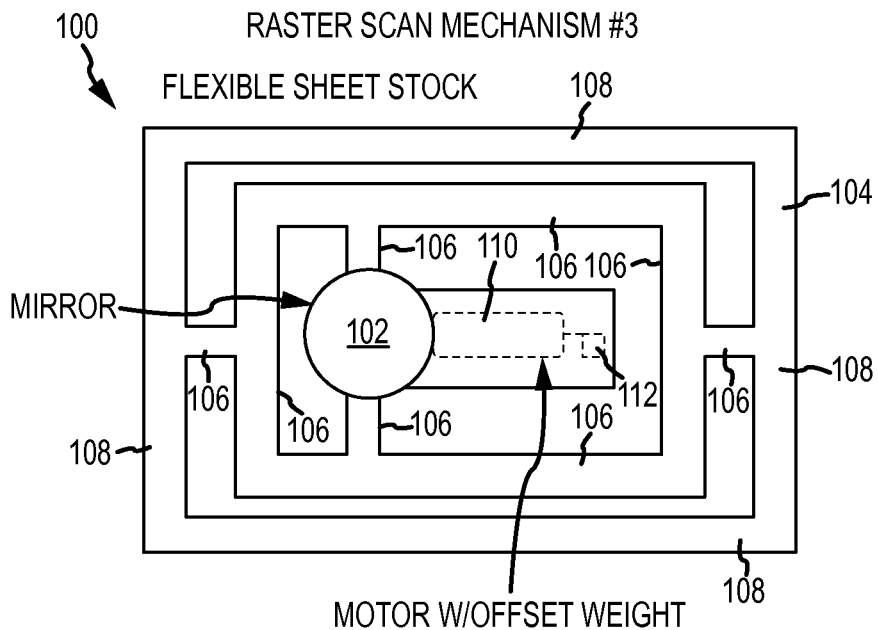
FIGS. 4 and 5 show yet another example implementation of an actuator assembly for moving an incident beam of a spectrometer across a surface of a sample.
Figure 5:
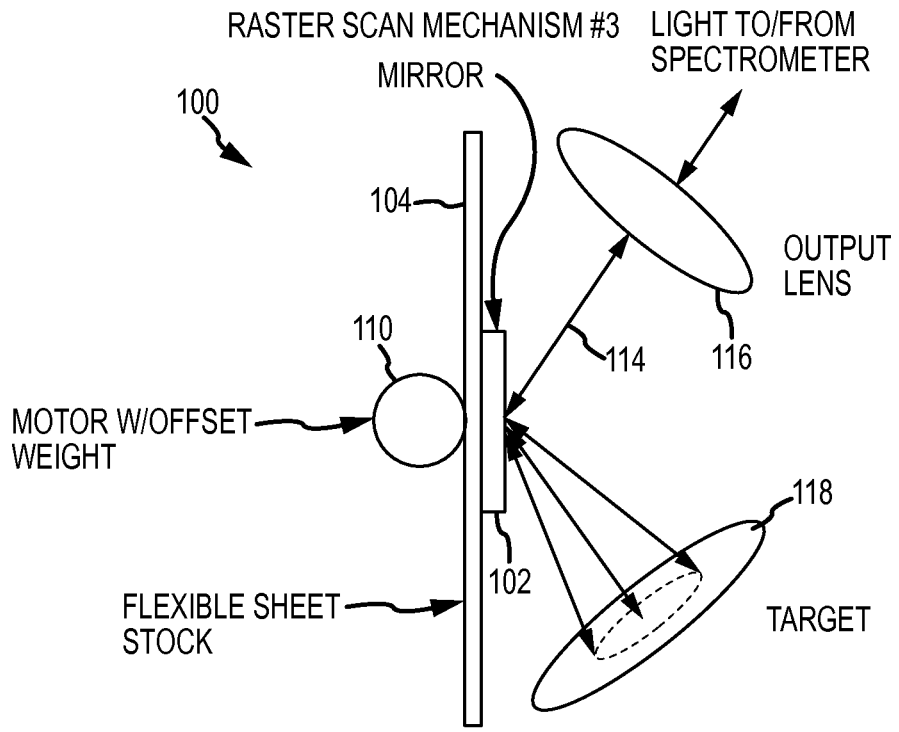

FIGS. 4 and 5 show yet another example implementation of an actuator assembly 100 for moving an incident beam of a spectrometer across a surface of a sample. FIG. 4 shows a top plan view of the actuator assembly 100, and FIG. 5 shows a side view of the actuator assembly 100. Similar to the actuator assemblies 60 and 80 shown in FIGS. 2 and 3, the actuator assembly 100 shown in FIGS. 4 and 5 moves one or more optical elements of a spectrometer (e.g., a moveable mirror) to scan, raster or otherwise move the incident beam across the surface of the sample.

In the implementation shown in FIG. 4, for example, an optical element, such as a mirror 102, is coupled to a flexible sheet stock 104. The flexible sheet stock 104 comprises a plurality of support members 106 coupled to perimeter edges 108 that are anchored. The support members 106 are able to move (e.g., oscillate) in response to an actuator such as a motor, magnet/coil pair or piezoelectric actuator. The support members 106 also support one or more optical elements of the spectrometer (such as mirror 102). The flexible sheet stock 104 may comprise any relatively flexible material. In one embodiment, for example, a 0.040 or 0.060 sheet of polystyrene may be used. Other relatively high modulus materials (e.g., brass) that are able to vibrate without unduly absorbing energy may also be used. Cut-outs in the flexible sheet stock 104, for example, may form the support members 106 of the actuator assembly. The cut-outs may be formed to create a particular bending or torsion profile when the motor 110 is activated.

As in FIGS. 2 and 3, the mirror 102 may correspond to the moveable mirror 32 shown in FIG. 1 or another mirror of the spectrometer. The perimeter edges 108 of the flexible sheet stock 104 may be anchored to allow the support members 106 to move (e.g., oscillate within the flexible sheet stock). In various embodiments, any number of the perimeter edges 108 (e.g., one, two, three, or all four edges of the flexible sheet) may be anchored in whole or in part. Although the flexible sheet stock 104 is shown anchored along the perimeter edges 108 and coupled to the mirror 102 at an internal support member 106, the flexible sheet stock 104 may be anchored and/or coupled to the mirror 102 at any location on the flexible sheet stock 104. As the support members 106 of the flexible sheet stock 104 flex, the mirror 102 is moved with respect to one or more other optical element, such as a focusing lens 116, of the spectrometer.

The flexible sheet stock 104 may be moved by any number of actuators. In the particular implementation shown in FIGS. 4 and 5, for example, a motor 110 comprising an offset weight 112 (e.g., a cell phone vibrator motor) is coupled to the flexible sheet stock 104. Two or more motors with offset weights may also be used. Multiple motors may be used, for example, to induce higher order oscillations in the support members of the flexible sheet stock 104. In the particular implementation shown in FIGS. 4 and 5, for example, the motor 110 is disposed on an opposite side of the flexible sheet stock 104 from the mirror 102. The motor 110, for example, may be offset from the mirror 102 as shown in FIG. 4 or directly opposing the mirror 102. In other implementations, however, the motor 102 can be disposed in virtually any location on the flexible sheet stock 104. The motor, for example, may be disposed on the same side of the flexible sheet stock 104 as the optical element (e.g., mirror 102). As the motor 110 is excited, the offset weight 112 vibrates the flexible sheet stock 104, moving the optical element (e.g., mirror 102) coupled to the flexible sheet stock 104.

In this implementation, the optical element comprises the mirror 102 that reflects an incident excitation beam 114 of the spectrometer. As shown in FIG. 5, the mirror 102 may be disposed between an output focusing lens 116 and a sample 118, similar to the arrangement shown in the implementation of FIG. 3, and reflect the incident beam from the output focusing lens 116 toward a sample 118. In another implementation, however, the mirror 102 may be disposed between an excitation source and the output focusing lens 116 of the spectrometer, similar to the arrangement of the implementation shown in FIG. 2 and reflect the incident beam through the output focusing lens 116 toward a sample 118.

By moving the mirror 102, the actuator assembly 100 moves the incident beam 114 across a surface of the sample 118. A spectroscopy signal induced at the sample by the incident beam 114 is received via the mirror 102 and either reflected to an output lens 116 of the spectrometer or passed through the mirror (e.g., for a dichroic beam-splitter mirror or a mirror with an aperture for receiving spectroscopy signals).

As described above with respect to FIGS. 2 and 3, the movement of the one or more optical elements coupled to the flexible sheet stock 104 can be controlled by applying one or more control signals to the motor 110. FIGS. 11 and 12, described below, show example control waveforms that can be used to control the motion of the optical element(s) and, in turn, the motion of the incident beam 114 across the surface of the sample 118.

The actuator assembly 100 may be used to move the incident beam across the surface of the sample in any number of patterns or paths. The actuator assembly 100, for example, may move the mirror 102 in a line, ellipse, circle or other controlled or uncontrolled manner to move the incident beam across the surface of the sample in any number of patterns or paths. The movement of the incident beam across the surface of the sample thus allows the spectrometer to sample a larger area of the sample without reducing the resolution of the spectrometer.

Figure 6:
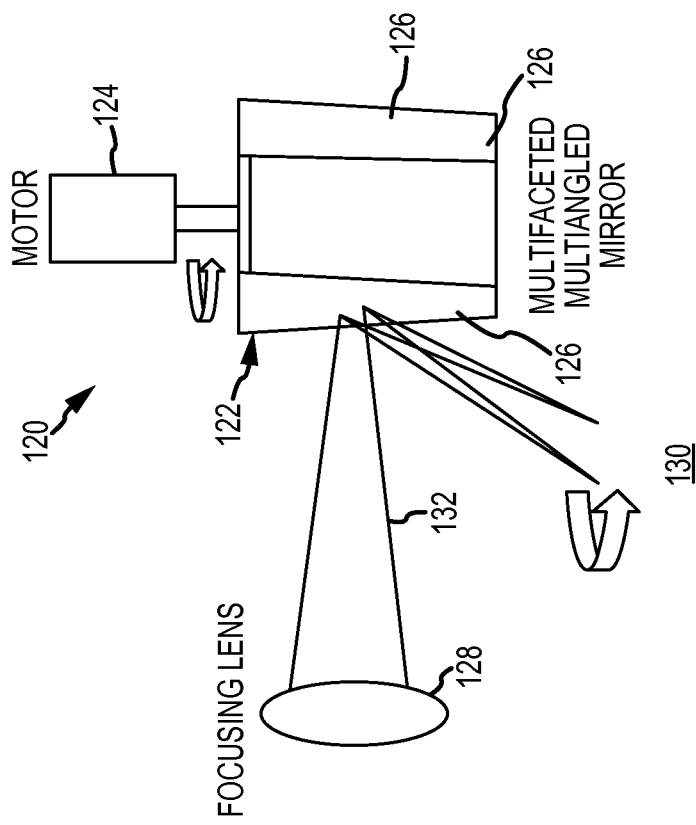
FIG. 6 shows yet another example implementation of an actuator assembly for moving an incident beam of a spectrometer across a surface of a sample.

FIG. 6 shows yet another example implementation of an actuator assembly 120 for moving an incident beam of a spectrometer across a surface of a sample. In this implementation, a multifaceted, multi-angled mirror assembly 122 is attached to a motor 124 configured to rotate the assembly to provide different faces 126 of the mirror assembly 122 to the optical system of a spectrometer to move an incident beam across a surface of a sample. Similar to the actuator assemblies shown in FIGS. 2-5, the actuator assembly 120 shown in FIG. 6 moves one or more optical elements (e.g., mirrors) of a spectrometer to scan, raster or otherwise move the incident beam across the surface of the sample.

The actuator assembly 120 shown in FIG. 6 is disposed between a focusing lens 128 of the spectrometer and the sample 130. The actuator assembly 120 receives the incident beam 132 from the focusing lens 128 and reflects the beam toward the sample 130. The actuator assembly 120 also receives a spectroscopy signal from the sample 130 and reflects it back to the optical system of the spectrometer via the focusing lens 128.

As the multiple facets 126 of the multi-faceted, multi-angled mirrors are rotated by the motor 124, the incident beam 132 (and a corresponding returning spectroscopy signal) may be directed in virtually any number of patterns or paths across the surface of the sample 130. In one implementation, for example, the multiple facets 126 of the actuator assembly 120 allow the incident beam 132 to trace multiple lines in a raster pattern similar to a cathode ray tube (CRT) raster pattern. As the mirror assembly 122 rotates, for example, each mirror 126 can direct an incident beam in a line across the sample 130, and as the next, differently angled mirror is rotated towards the incident beam 132, the different angle of the mirrors can direct the incident beam 132 in consecutive lines across the surface of the sample 130. Other mirror angles and facets can also be used to direct the incident beam across the surface of the sample in different patterns or paths.

Figure 7:
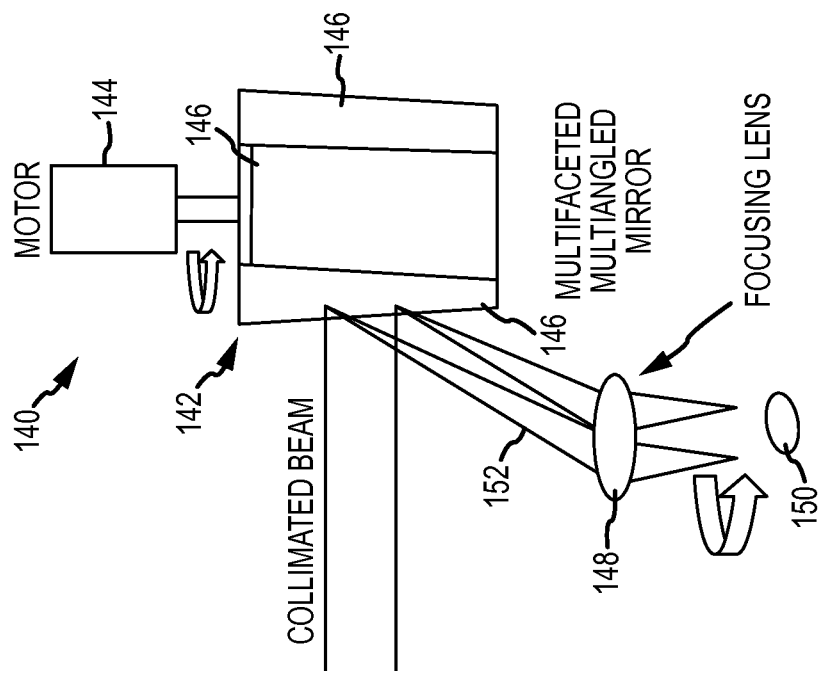
FIG. 7 shows another example implementation of an actuator assembly for moving an incident beam across a surface of a sample.

FIG. 7 shows another example implementation of an actuator assembly 140 for moving an incident beam across a surface of a sample. Similar to the implementation shown in FIG. 6, the implementation of FIG. 7 comprises a multifaceted, multi-angled mirror assembly 142 attached to a motor 144 configured to rotate the assembly 142 to provide different faces 146 of the mirror assembly 142 to the optical system of a spectrometer to move an incident beam 152 across a surface of a sample 150. Similar to the actuator assemblies shown in FIGS. 2-6, the actuator assembly 140 shown in FIG. 7 moves one or more optical elements (e.g., mirrors 146) of a spectrometer to scan, raster or otherwise move the incident beam 152 across the surface of the sample 150.

The actuator assembly 140 shown in FIG. 7 is disposed between an excitation source of a spectrometer and a focusing lens 148 of the spectrometer. The actuator assembly 140 receives the incident beam 152 via the excitation source directly or indirectly (e.g., in a collimated beam) and reflects the beam 152 toward the focusing lens 148, which in turn focuses the incident beam 152 on the sample 150. The actuator assembly 140 also receives a spectroscopy signal via the focusing lens 148 and redirects it to the optical system of the spectrometer.

Similar to the actuator assembly of FIG. 6, the actuator assembly 140 of FIG. 7 can be designed to direct an incident beam of a spectrometer across the surface of a sample in any number of patterns, such as in a raster pattern similar to a CRT raster pattern.

FIG. 7A shows yet another example implementation of an actuator assembly 120A for moving an incident beam of a spectrometer across a surface of a sample. In this implementation, an angled mirror assembly 122A is attached to a drive shaft 125A of a motor 124A. The motor 124A, for example, can be configured to rotate a rotary drive shaft to rotate the assembly angled mirror assembly 122A, in turn. Rotating the angled mirror assembly 122A moves a face 126A of the angled mirror assembly 122A with respect to the incident beam (e.g., a laser or other light beam). As the face 126A of the mirror assembly 122A is rotated, the incident beam is redirected to the surface of the sample and is moved across the surface of the sample. In the implementation shown in FIG. 7A, for example, the incident beam can be directed in a generally circular, generally oval, circular, oval or other shaped pattern across the surface of the sample. Similar to the actuator assemblies shown in FIGS. 2-7, the actuator assembly 120A shown in FIG. 7A moves one or more optical elements (e.g., mirrors) of a spectrometer to scan, raster or otherwise move the incident beam across the surface of the sample.

In the particular example shown in FIG. 7A, for example, the angled mirror assembly 122A is disposed at an angle 127A with respect to the drive shaft 125A of the motor 124A that is not perpendicular to the drive shaft 125A. In this example, where the incident beam is directed off-center to the face 126A of the mirror assembly 122A, the incident beam is moved across the surface of the sample as the mirror assembly 122A is rotated by the drive shaft 125A of the motor 124A. Where the mirror assembly 122A is generally rigid and fixedly mounted on the drive shaft 125A, for example, the incident beam will be moved across a surface of the sample in a generally circular pattern. The pattern, however, may be altered by changing the angle 127A, by mounting the mirror assembly 122A to the drive shaft 125A so that the mirror assembly 122A is able to wobble or otherwise move with respect to the drive shaft 125A, by flexibly mounting the mirror assembly 122A to the drive shaft 125A (e.g., by one or more springs or other flexible mounts such as a flexible substrate or sheet stock shown and described herein with respect to FIGS. 4 and 5), and/or the motor 124A may be flexibly mounted within or to a spectrometer such as via one or more springs or other flexible mounts. Where the mirror assembly 122A and/or the motor 124A is flexibly mounted, the mirror assembly 122A may be mounted to the drive shaft so that the mirror face 126A is generally perpendicular to the drive shaft, but able to move the incident beam with respect to a surface of the sample as the mirror face 126A is moved (e.g., vibrated) with respect to the incident beam.

The mirror assembly 122A may also be automatically reset to a fixed position so that the incident beam may be reliably directed to a single, predetermined location for taking a spectrum of the sample at a fixed location. In one implementation, for example, a pair of magnets 127A, 129A may be attached to the mirror assembly 122A and/or the drive shaft 125A of the motor 124A. The magnets 127A, 129A, for example, may include permanent and/or electromagnets that may move the mirror assembly 122A into a set, predetermined position with respect to the incident beam. Thus, when a spectrum is to be taken at a set, stationary position at the sample, the pair of magnets 127A, 129A may attract each other and lock the mirror assembly in the predetermined position. However, the incident beam may also be moved with respect to a surface of the sample when the drive shaft 125A is rotated. In one implementation, for example, the pair of magnets 127A, 129A provide sufficient strength to move the mirror assembly 122A into the set, predetermined location when the drive shaft 125A is not rotated by the motor 124A, but the motor 124A is powerful enough to overcome the strength of the pair of magnets 127A, 129A so that the motor 124A can rotate the drive shaft and the mirror assembly 122A. In another embodiment, one or both of the magnets 127A, 129A may be an electromagnet that may be activated when the mirror assembly 122A is to be locked in the set, predetermined location and deactivated when the mirror assembly 122A is to be moved with respect to the incident beam.

In another implementation, the pair of magnets may instead comprise a single magnet and another component that may be magnetically coupled with the single magnet. For example, a material that may be coupled (e.g., iron) to the magnet may be used in place of one of the magnets described above. In one implementation, for example, a magnet may be coupled to the drive shaft and/or the rotating mirror assembly of the actuator and a fixed element that is configured to magnetically couple with the magnet. In this implementation, the magnet physically coupled to the drive shaft and/or rotating mirror assembly may turn the drive shaft and/or rotating mirror assembly until the magnet is positioned adjacent to the fixed element to set the mirror face and the rotating mirror assembly at a set, predetermined position. Alternatively, a magnet may be fixed within and/or to the spectrometer and be configured to magnetically couple to an element physically fixed to the drive shaft and/or the rotating mirror assembly of the actuator. In this implementation, the magnet will draw the fixed element of the actuator towards the magnet until they are disposed adjacently to each other and the mirror face and/or the rotating mirror assembly are at a set, predetermined position.

Figure 7B:
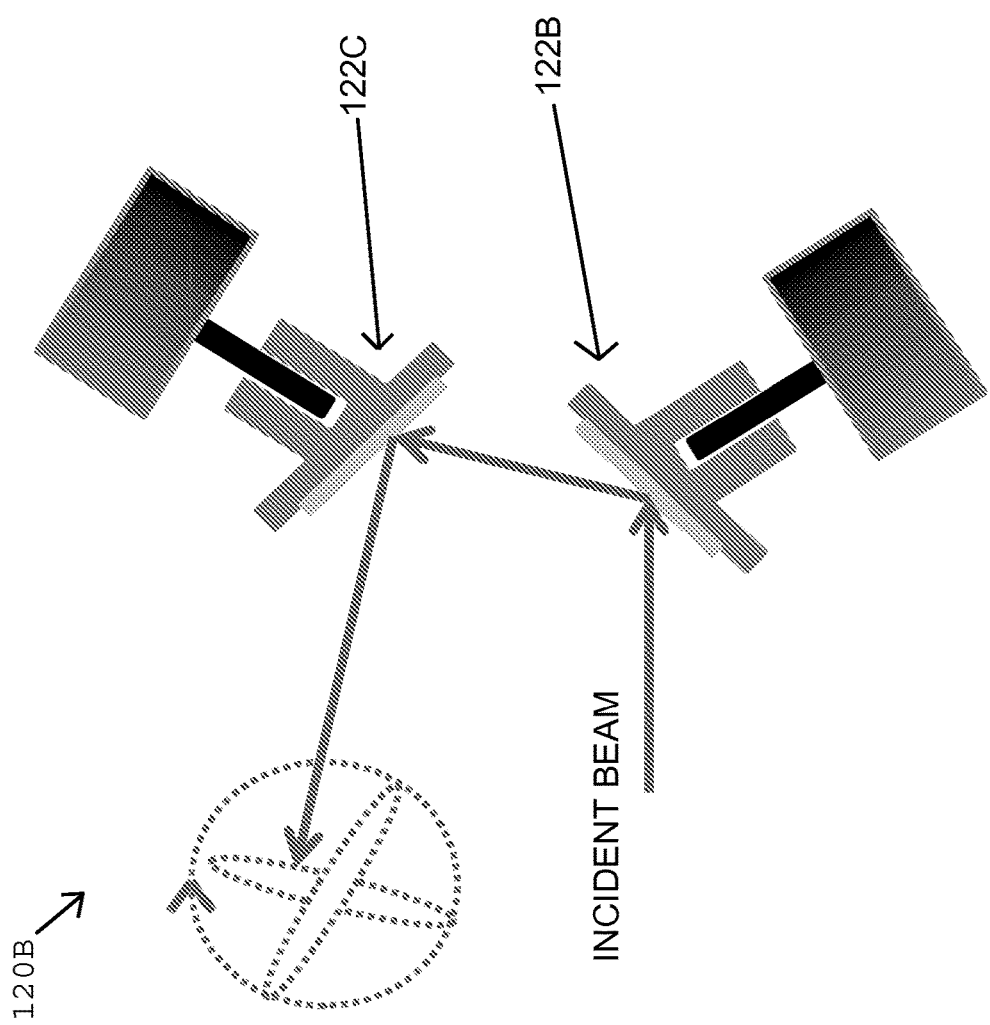

FIG. 7B shows another implementation in which two or more rotating mirror assemblies 122B, 122C are used to direct an incident beam to a sample. The rotating mirror assemblies may each be assemblies such as shown and described with respect to FIG. 7A and may be arranged in any number of configurations. In the particular implementation shown in FIG. 7B, for example, two rotating mirror assemblies 122B and 122C are arranged so that an incident beam is directed to a first rotating mirror assembly 122B, then to a second rotating mirror assembly 122C and then to the sample. In this implementation, the incident beam is redirected by the first rotating mirror assembly 122B so that the redirected incident beam is moved with respect to a mirror face of the second mirror assembly 122C, such as in a circular or oval pattern. In this implementation, for example, the rotating mirror assemblies 122B and 122C include an angled mirror face 126B, 126C disposed at a non-perpendicular angle with respect to drive shafts of the respective assemblies.

As shown in FIG. 7B as the pair of rotating mirror assemblies 122B, 122C are rotated as described above, the incident beam is moved in a series of oval patterns within a generally circular pattern to take a illuminate the sample across a surface of the sample within the larger generally circular pattern. Although particular patterns are shown and described, any number of patterns or even non-patterned movements may be achieved depending on the construction and arrangement of the actuator assembly 120B as described above with respect to FIG. 7A any component of the actuator assembly 120B may be flexibly or otherwise movably mounted so that vibration, wobbling or other movement of the component(s) may alter the movement of the incident beam at the sample.

As described above with respect to FIGS. 6 and 7, the actuator assembly 120A or 120B shown in FIGS. 7A and 7B may be disposed between a focusing lens 128 of the spectrometer and the sample 130 (such as shown in FIG. 6) or may be disposed between an excitation source and a focusing lens of a spectrometer. In either implementation, the actuator assembly 120A or 120B receives the incident beam (from the focusing lens or the excitation source) and reflects the beam toward the sample. The actuator assembly also receives a spectroscopy signal from the sample and reflects it back to the optical system of the spectrometer.

As described with respect to FIG. 7A, the actuator assembly 120B may further include a pair of magnets to move the rotating mirror assemblies 122B and 122C into a set, predetermined position. Similarly, the motors (either in FIG. 7A or 7B) may be configured to move the assemblies into a predetermined position such as via a stepper or other motor that can be configured to do so. In addition, although shown with respect to FIGS. 7A and 7B, similar magnetic configurations may be used with respect to the other actuator assemblies shown and described herein. With respect to various flexible beam or flexible sheet stock implementations shown in FIGS. 1-5 and 8-10, a first magnet may be attached to the flexible beam (e.g., at or near the distal end of a flexible beam) or flexible sheet stock (e.g., at or near where the mirror is affixed to the flexible sheet stock) and a second magnet may be secured within and/or to the spectrometer to attract and hold the flexible beam or flexible sheet stock in a set, predetermined position. With respect to the rotating multi-faceted multi-angled mirror implementations shown in FIGS. 6 and 7, a pair of magnets may be arranged in a substantially similar manner as shown and described with respect to FIGS. 6 and 7.

Figure 8:
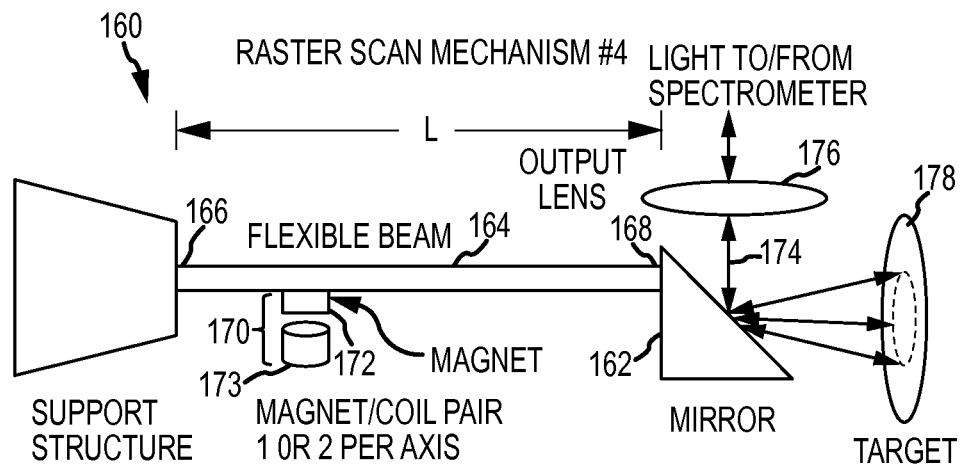
FIG. 8 shows yet another example implementation of an actuator assembly for moving an incident beam of a spectrometer across a surface of a sample.

FIG. 8 shows yet another example implementation of an actuator assembly 160 for moving an incident beam of a spectrometer across a surface of a sample. Similar to the actuator assemblies shown in FIGS. 2-7, the actuator assembly 160 shown in FIG. 8 moves one or more optical elements of a spectrometer to scan, raster or otherwise move the incident beam across the surface of the sample.

In the particular implementation shown in FIG. 8, a mirror 162 (or other optical element) is coupled to a flexible beam 164. The mirror 162 may correspond to the moveable mirror 32 shown in FIG. 1. A first proximal end 166 of the flexible beam 164 is anchored and a second distal end 168 of the flexible beam 164 is coupled to the mirror 162. Again, although the flexible beam is shown anchored at the first proximal end 166 and coupled to the mirror 162 at the second distal end 168, the flexible beam 164 may be anchored and/or coupled to the mirror 162 at any point along a length L of the flexible beam 164. As the beam 164 flexes, the mirror 162 is moved with respect to one or more other optical element, such as a focusing lens 176, of the spectrometer.

The flexible beam 164 may be moved by any number of actuators. In the particular implementation shown in FIG. 8, for example, a magnet/coil pair 170 is provided to move the flexible beam 164 and the optical element (e.g., mirror 162) coupled to the beam 164. In the implementation, shown in FIG. 8, for example, a magnet 172 (e.g., a permanent magnet) of the magnet/coil pair 170 is coupled to the flexible beam 164 offset from the anchor point of the flexible beam 164 (e.g., the first proximal end 166). A coil 173 of the magnet/coil pair 170 is disposed adjacent to the magnet 172 and can be controlled to repel and/or attract the magnet 172 coupled to the beam 164. Although the magnet 172 is shown coupled to the flexible beam 164 and the coil 173 is shown offset from the beam 164 and the magnet 172, the opposite may also provided (i.e., the coil may be coupled to the beam 164 and the magnet 172 may be offset from the beam 164 and the coil 173). As a current is applied to the coil 173, the opposing magnet 172 may be repelled and/or attracted to move the flexible beam 164, and, in turn, move the optical element (e.g., the mirror 162) coupled to the flexible beam 164. In this implementation, the optical element comprises the mirror 162 that reflects an incident excitation beam 174 from an output lens 176 of the spectrometer towards a sample 178. By moving the mirror 162, the actuator assembly 160 moves the incident beam 174 across a surface of the sample 178. A spectroscopy signal induced at the sample 178 by the incident beam 174 is received via the mirror 162 and either reflected to the output lens 176 of the spectrometer or passed through the mirror (e.g., for a dichroic beam-splitter mirror or a mirror with an aperture for receiving spectroscopy signals). Similarly, the mirror 162 may also be disposed between an excitation source and the focusing lens 176 as shown in FIG. 2.

As described above with respect to FIGS. 2-5, the movement of the one or more optical elements coupled to the flexible beam 164 can be controlled by applying one or more control signals to the magnet/coil pair 170. FIGS. 11 and 12, described below, show example control waveforms that can be used to control the motion of the optical element(s) and, in turn, the motion of the incident beam 174 across the surface of the sample 178.

Figure 9:
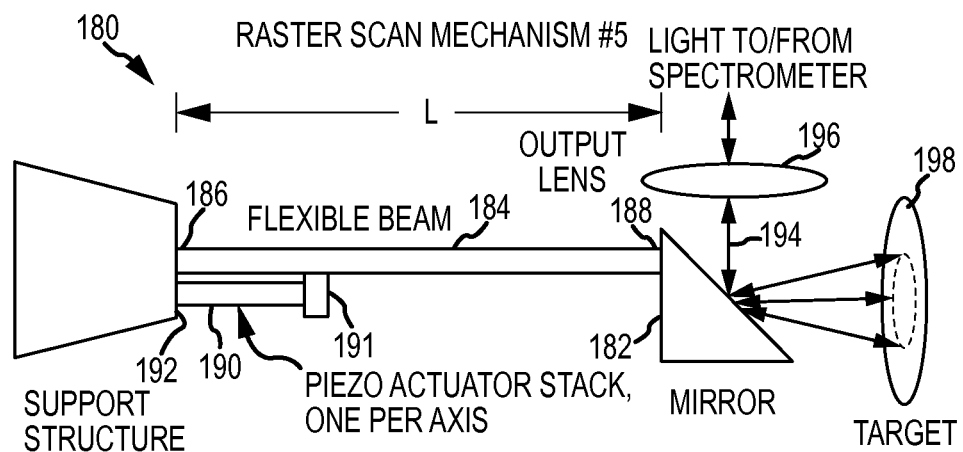
FIG. 9 shows another example implementation of an actuator assembly for moving an incident beam of a spectrometer across a surface of a sample.

FIG. 9 shows another example implementation of an actuator assembly 180 for moving an incident beam of a spectrometer across a surface of a sample. Similar to the actuator assemblies shown in FIGS. 2-8, the actuator assembly 180 shown in FIG. 9 moves one or more optical elements of a spectrometer to scan, raster or otherwise move the incident beam across the surface of the sample.

In the particular implementation shown in FIG. 9, a mirror 182 (or other optical element) is coupled to a flexible beam 184. The mirror 182 may correspond to the moveable mirror 32 shown in FIG. 1. A first proximal end 186 of the flexible beam 184 is anchored and a second distal end 188 of the flexible beam 184 is coupled to the mirror 182. Again, although the flexible beam 184 is shown anchored at the first proximal end 186 and coupled to the mirror 182 at the second distal end 188, the flexible beam 184 may be anchored and/or coupled to the mirror 182 at any point along a length L of the flexible beam 184. As the beam 184 flexes, the mirror 182 is moved with respect to one or more other optical element, such as a focusing lens 196, of the spectrometer.

The flexible beam 184 may be moved by any number of actuators. In the particular implementation shown in FIG. 9, for example, a piezoelectric actuator 190 (e.g., a piezoelectric actuator stack) is provided to move the flexible beam 184 and the optical element coupled to the beam 184. In this implementation, for example, the piezoelectric actuator 190 is coupled to the flexible beam 184 at a location 191 offset from the anchor point of the flexible beam 184 (e.g., the first proximal end 186). The piezoelectric actuator 190 is also anchored at a location 192 opposing where the piezoelectric actuator 190 is coupled to the flexible beam 184. The piezoelectric actuator 190 can be controlled to move the flexible beam 184 (e.g., by flexing the beam 184). The flexible beam, in turn, moves the optical element coupled to the flexible beam 184. In this implementation, the optical element comprises the mirror 182 that reflects an incident excitation beam 194 from an output lens of the spectrometer towards a sample 198. By moving the mirror 182, the actuator assembly 180 moves the incident beam 194 across a surface of the sample 198. A spectroscopy signal induced at the sample 198 by the incident beam 194 is received via the mirror 182 and either reflected to the output lens 196 of the spectrometer or passed through the mirror (e.g., for a dichroic beam-splitter mirror or a mirror with an aperture for receiving spectroscopy signals). Similarly, the mirror 182 may also be disposed between an excitation source and the focusing lens 196 as shown in FIG. 2.

As described above with respect to FIGS. 2-5, the movement of the one or more optical elements coupled to the flexible beam 184 can be controlled by applying one or more control signals to the piezoelectric actuator 190. FIGS. 11 and 12, described below, show example control waveforms that can be used to control the motion of the optical element(s) and, in turn, the motion of the incident beam 194 across the surface of the sample 198.

Although the actuators of FIGS. 8 and 9 are shown with respect to a flexible beam, the actuators may alternatively be provided with one or more flexible sheet stocks, such as shown with respect to FIGS. 4 and 5.

Figure 10:
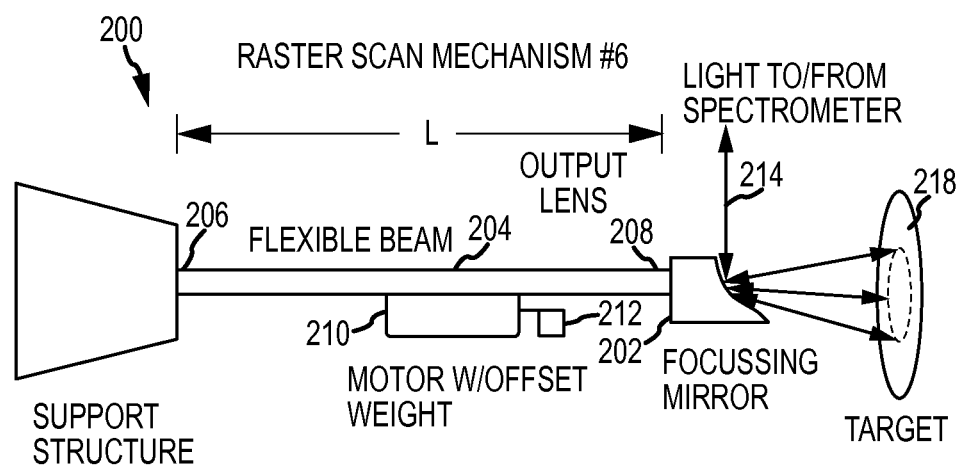
FIG. 10 shows yet another example implementation of an actuator assembly 200 for moving an incident beam of a spectrometer across a surface of a sample.

FIG. 10 shows yet another example implementation of an actuator assembly 200 for moving an incident beam of a spectrometer across a surface of a sample. Similar to the actuator assemblies shown in FIGS. 2 and 3, the actuator assembly 200 shown in FIG. 10 moves one or more optical elements of a spectrometer to scan, raster or otherwise move the incident beam across the surface of the sample.

In the particular implementation shown in FIG. 10, a focusing mirror 202 (or other optical element) is coupled to a flexible beam 204, such as described above with respect to FIGS. 2 and 3. The focusing mirror 202 may correspond to a combination of the moveable mirror 32 and the output focusing lens 34 shown in FIG. 1. Thus, the focusing mirror 202 both focuses the incident beam 214 and moves the beam 214 across a surface of the sample 218. A first proximal end 206 of the flexible beam 204 is anchored and a second distal end 208 of the flexible beam 204 is coupled to the mirror 202. Again, although the flexible beam 204 is shown anchored at the first proximal end 206 and coupled to the mirror 202 at the second distal end 208, the flexible beam 204 may be anchored and/or coupled to the mirror 202 at any point along a length L of the flexible beam 204. As the beam 204 flexes (e.g., due to force bending and/or torsion), the focusing mirror 202 is moved with respect to one or more other optical element of the spectrometer. The movement of the beam 204, for example, may alter an angle of the focusing mirror 202 and redirect the incident beam from a static path. A collimated incident beam (received via an optical system of the spectrometer), for example, hits the focusing mirror 202 and is focused and redirected to form a focused spot or area on the sample 218. As described above with respect to FIGS. 2 and 3, the size and shape of an area being illuminated on the sample 218 can be changed with motor speed, beam shape, beam stiffness, and the like. In addition, a speed of the motor 210 can be changed (e.g., ramped) in a fashion to maximize the illuminated area.

The flexible beam 214 may be moved by any number of actuators. In the particular implementation shown in FIG. 10, for example, a motor 210 comprising an offset weight 212 (e.g., a cell phone vibrator motor) is coupled to the flexible beam 204 offset from the anchor point of the flexible beam 204 (e.g., the first proximal end 206). As the motor is excited, the offset weight 212 vibrates the flexible beam 204, moving the optical element (e.g., the focusing lens 202) coupled to the flexible beam 204. In this implementation, the optical element comprises the focusing mirror 202 that focuses and reflects an incident excitation beam 214 from the spectrometer optical system towards a sample 218. By moving the mirror 202, the actuator assembly 200 moves the incident beam 214 across a surface of the sample 218. A spectroscopy signal induced at the sample by the incident beam 214 is received via the mirror 202 and either reflected to the spectrometer optical system or passed through the mirror 202 (e.g., for a dichroic beam-splitter mirror or a mirror with an aperture for receiving spectroscopy signals).

As described above with respect to FIGS. 2 and 3, the movement of the one or more optical elements coupled to the flexible beam 204 can be controlled by applying one or more control signals to the motor 210. FIGS. 11 and 12, described below, show example control waveforms that can be used to control the motion of the optical element(s) and, in turn, the motion of the incident beam 214 across the surface of the sample 218.

The actuator assembly 200 may be used to move the incident beam across the surface of the sample 218 in any number of patterns or paths. The actuator assembly 200, for example, may move the mirror 202 in a line, ellipse, circle or other controlled or uncontrolled manner to move the incident beam across the surface of the sample in any number of patterns or paths. The movement of the incident beam across the surface of the sample thus allows the spectrometer to sample a larger area of the sample 218 without reducing the resolution of the spectrometer.

FIGS. 11 and 12 show waveforms of example motor drive waveforms that may be used to control the motors of the implementations shown in FIGS. 2-5 and 10. FIG. 11, for example, shows a sawtooth motor drive waveform 220 that may be used as a control signal for a motor of an actuator assembly. The sawtooth motor drive waveform includes an initial power boost portion 222 and a speed control ramp portion 224. FIG. 11 shows a triangle motor drive waveform 230 that may also be used as a control signal for a motor of the actuator assembly. The triangle motor drive waveform 230 includes an initial power boost portion 232 and a speed control ramp portion 234. These example waveforms may be used to vary a motor speed in a controlled fashion. Since DC motors run at a lower speed (or voltage) than they will start at, a control signal may provide an initial spike and then switch to a controlled ramp signal.

Varying the speed of the DC motor can collapse a pattern (e.g., a circular or elliptical pattern) such that the incident beam may be moved over an entire pattern instead of merely around a perimeter of a pattern.

Other actuators may also be driven in various manners to achieve movement of the incident beam across the surface of the sample in various patterns or paths. A magnet/coil pair actuator, such as shown in FIG. 8, could be driven by a control signal, such as a square wave or sine wave control signal. A piezoelectric actuator such as shown in FIG. 9 could also be driven by a control signal, such as a sine wave. A sine wave control signal, for example, could be varied in amplitude and/or frequency to vary the motion of the actuator assembly.

Figure 13:
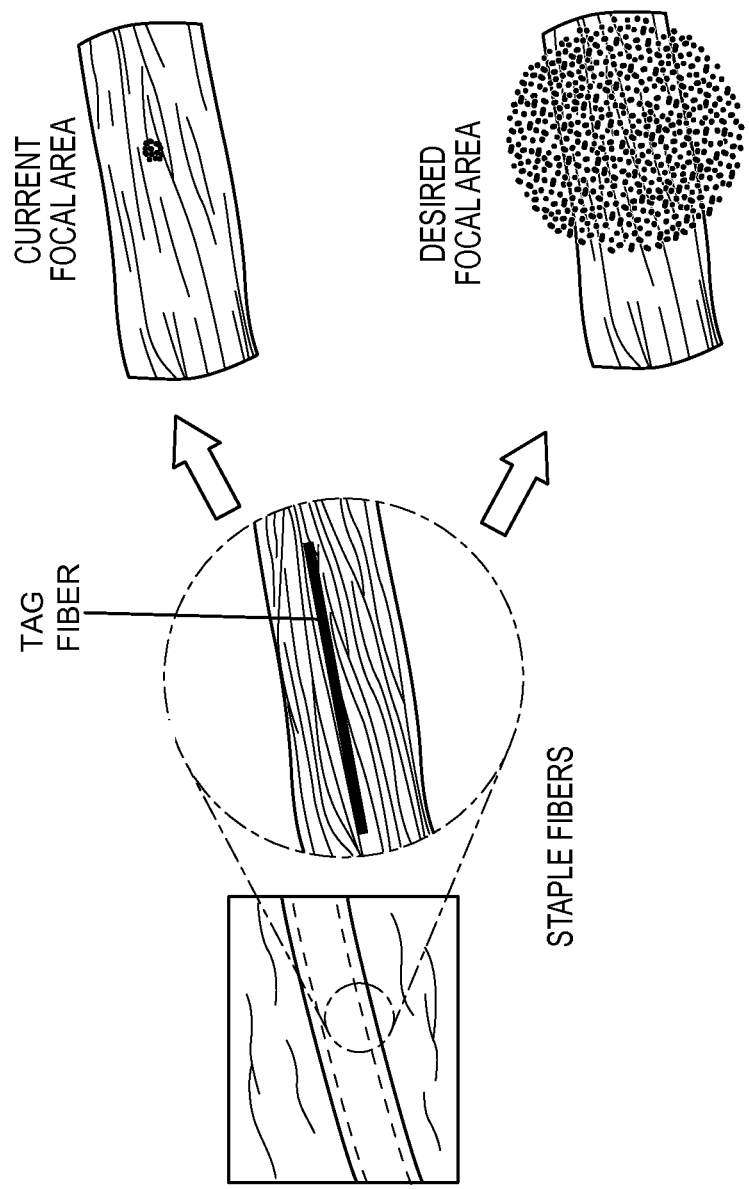
FIG. 13 shows example focal areas for a spectrometer.

While studies of Raman targets can be performed on various equipment, such as on a combination of a very high end Renishaw Raman microscope and a moderately priced commercial-of-the-shelf (COTS) hand-held Raman system, detecting small targets disposed within a larger target area can be difficult. In a textile environment in which one or more tagged fibers (e.g., yarns) are disposed within a larger textile product, a moderately priced COTS Raman device can be used to authenticate tagged yarns; however, design changes are provided to provide a more viable thin line-based textile authentication solution (FIG. 13).

A COTS Raman reader such as described above may use sampling probes that provide moderate control of the focal distance between the system and sample (e.g., to identify unknown bulk materials (powders, pure liquids, etc.)). Bulk material identification does not typically require precise location of the sample. Further, the identification of unknowns requires high spectral resolution and an associated small sampling/focal volume (50 μm). In one implementation, for example, difficulties associated with Raman analysis of irregular thin line samples using small focal volumes include difficulty of locating and focusing on fibrous substrates that are made of individual fibers having diameters between 10-30 μm.

In one implementation of a detector, a Raman spectrometer, as provided herein, may be used to detect tagged fibers blended within a textile product (e.g., blended thin lines, such as having only 1-3% active fibers). In one implementation, a Raman reader equipped with scanning capabilities and an expanded focal volume (e.g., 100 s of μm) is provided.

A Raman reader for thin-line based textile authentication, with a low-cost, easy to use handheld device is provided in one implementation. The challenges for designing a viable commercial reader to couple with a small tagged item within a larger sampling area include a sampling mechanism and a cost/performance benefit to the end user.

In one implementation, for example, a unique high étendue excitation/collection system and spectrometer design is provided.

Étendue relates to the light collection, but better than simply expressing the solid angle of light collected, étendue includes the spectral resolution as well. This can be seen from the approximation for the étendue (G), $G=S'L/q$, where $S'$ is the slit width, L is the area of the collection lens, and q is the distance from the collection lens to the entrance slit. See, e.g., www.horiba.com/us/en/scientific/products/optics-tutorial/throughput-etendue/. This concept accounts for the width of the entrance slit, which in a 1:1 imaging spectrograph, and equates to the spectral resolution and it accounts for the area of the lens and magnification through the L/q term.

A typical modern Raman system attempts to produce a small spot at the sample such that the collection lens can collect a large solid angle, magnify the spot, and send it through a narrow slit to maintain a reasonable resolution. This is ideal for homogeneous bulk samples. As indicated above, certain detection solutions, however, require a different set of standards. The sample, a thread on an item of clothing, for example, is not representative of a homogeneous sample and the end users, under the repetitious demands of continual testing, cannot be assumed to be capable of careful point and shoot accuracy to hit the correct thread. This requires the reader to sample a large area, which on a typical material identification system would mean a large spot size at the sample and as the étendue concept suggests, a large slit with and concomitant poor spectral resolution. This may be acceptable with a very limited number of tags, but it is incompatible with the spectral resolution required to resolve many tags (e.g., 100 s to 1000 s of tags) that may be present in various implementations.

Figure 14:
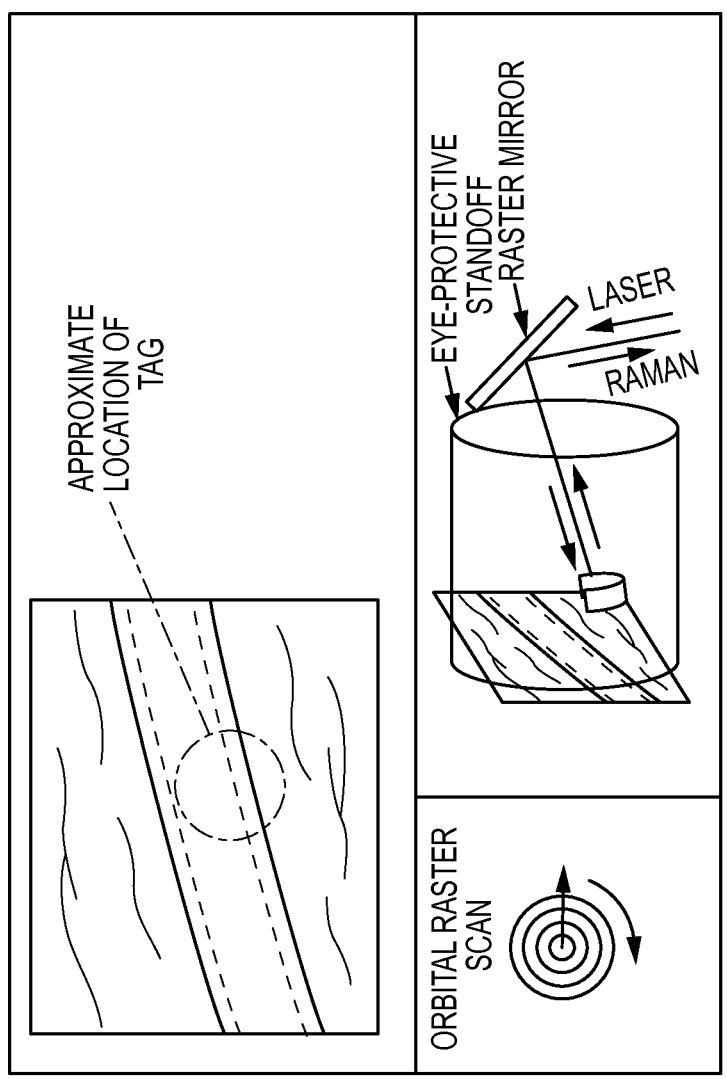
FIG. 14 shows an example implementation to detect a fiber authentication tag.

FIG. 14 illustrates one implementation of a solution to this problem. In this implementation, the reader is designed to raster the tightly focused laser excitation beam, which couples the Raman excitation from that beam to a narrow slit width for good spectral resolution, and maintains high spectral throughput with a low f/# collection lens and spectrograph. Rather than using a large spot size, the orbital raster scan (ORS™) maintains a small beam size to aperture design. The net effect is an averaged spot size that allows the end user to place the device near the thread of interest and scan an area large enough to enclose the thread. The difference between this design and currently available Raman systems is significant; with ORS™, high spectral resolution and therefore Raman resolving power will be retained for a plurality (e.g., 1000+) tags to be detected in various systems.

Laser safety End user considerations also control the focus of the reader. Various other material identification systems use contact probes to insure best focus. Where samples are homogenous powers, solids, or liquids, for example, these systems use a pointed tip or a vial holder. For a first defender in full HAZMAT this is a very appropriate design. However, it is not ideal for locating a tagged device (e.g., a tagged fiber on a piece of clothing).

In one implementation, the reader focus can be located away from (e.g., 25 mm away) a collection lens and to cover the sampling distance with a tube of protective material (e.g., plastic). The material (e.g., plastic) can be smoked to produce an overall absorbance or may be wavelength selective to allow good visibility of the sample and still provide absorption at the proposed 808 nm wavelength laser.

In this implementation, the system will allow unskilled end-users to operate the device without concerns over focusing or eye-safety, while observing the area that is illuminated. The eye-safety cylinder can be interlocked such that the laser is only on when pressure is applied to the sample. This provides laser safety to the user.

Library matching and resolution In a typical library matching algorithm, a simple correlation, is represented by:

$$R^2=1-(<L_m>\cdot<U_m>)^2/[(<L_m>\cdot<L_m>)(<U_m>\cdot<U_m>)]$$

where, $L_m$ and $U_m$ are the mean-centered library and sample (unknown) spectra, respectively. This method works very well for searching large databases. One characteristic of this algorithm is high sensitivity to the frequency position of the Raman features and less sensitivity to the relative peak intensities. Mean-centering removes spurious results due to variations in the spectral baselines.

Figure 15:
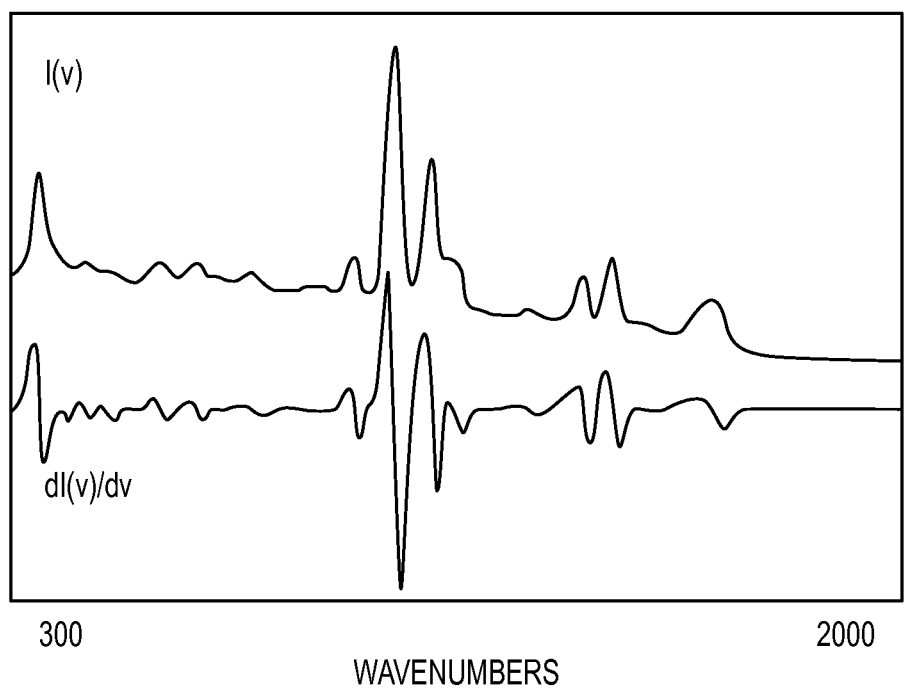
FIG. 15 shows an example spectrum and first derivative of the spectrum for a fiber authentication tag.

Fluorescence can cause problems with this routine, as the fluorescence background is not removed by mean-centering. To correct for fluorescence a first derivative spectrum can be taken. This removes the low frequency intensity changes due to fluorescence while producing sharp peaks for the high frequency Raman bands (FIG. 15).

McCreery, R., Horn, A., Spencer, J., and Jefferson, E., 1998, Noninvasive identification of materials inside USP vials with Raman spectroscopy and a Raman spectral library. J. Pharm. Sci., 87(1), 1-8 is a reference for realistic material matching with Raman spectroscopy. This reference illustrates the large enhancement of matching with a first derivative correlation; it illustrates the relative resistance of the matching algorithms to SNR reduction. For example, they show excellent matching ($R^2=0.95$) with a signal to noise of 17. Even with a signal to noise of 2.8 the matching algorithm still properly identified the material.

The spectrum in FIG. 15 of an activated thread was acquired in 1 second with a system to be described below. Table 1 illustrates calculated and anticipated SNR values for tags. In this table the SNR is presented in two formats: as a single peak measurement, and as a full spectral matching measurement. Actual SNR comparison of the single peak and full spectral matching is presented from the second column on the left; the full spectral matching is nearly 4 times better SNR than a single peak. In one implementation, a system may be able to positively identify a thin, tagged fiber using an approximate 2% blend of the tagged fiber within a textile product. The next columns show how the SNR is affected by this dilution and by rastering to produce a larger spot and changing the integration to 10 seconds. If a threshold of SNR >5 is established it can be seen that a low powered laser system is well above that for area (full spectral) matching and if a higher powered (80 mW laser) is used then we are 12 times above the threshold.

performance nearly equivalent to systems with a high powered laser and expensive scientific grade detector. These results appear contrary to established Raman performance; but it is important to understand various implementations that may be achieved. In certain implementations, for example, readers are operated in the less than 10 second acquisition regime. In this regime, dark noise is not significant and a low cost, low readout noise detector can perform as well as expensive highly cooled detectors.

SERS Nanoparticle Active Fiber Readers

Challenges for a viable commercial reader to couple with SERS nanoparticle active fiber targets include the sampling mechanism and the cost/performance benefit to the end user. These challenges can be met with a unique high étendue excitation/collection system of a spectrometer design described herein.

Étendue

Étendue relates to the light collection, but better than simply consisting of the solid angle of light collected, étendue includes the spectral resolution as well. This can be seen from the approximation for the étendue (G), $G=S'L/q$, where $S'$ is the slit width, L is the area of the collection lens, and q is the distance from the collection lens to the entrance slit. This concept nicely accounts for the width of the entrance slit which in a 1:1 imaging spectrograph is equivalent to the spectral resolution and it accounts for the area of the lens and magnification through the L/q term.

A typical modern Raman system attempts to produce a small spot at the sample such that the collection lens can collect a large solid angle, magnify the spot, and send it through a small slit to maintain a reasonable resolution. Handheld material identification systems work well under these requirements when the samples are homogeneous.

In one implementation, a different set of standards is provided. A sample (e.g., a thread on an item of clothing) is not representative of a homogeneous sample. An end user, under the repetitious demands of continual testing, cannot be assumed to be capable of careful point and shoot accuracy to hit the correct thread. This requires the reader to sample a large area, which on a typical material identification system could mean a large spot size at the sample and as the étendue concept suggests, a large slit with and concomitant poor spectral resolution. This may be acceptable with a very limited number of tags, but it is incompatible with the

TABLE 1

SNR calculated for blended thin lines using the various SnRI Raman reader configurations
Example Raman reader design

| | Power | | | | |
|---|---|---|---|---|---|
| | 15 mW Laser | 15 mW Laser | 15 mW Laser | 15 mW Laser | 80 mW Laser |
| Sample | Pure | 2% | 2% | 2% | 2% |
| Time/Spot size | SNR (1 second, 200 μm spot) | SNR (1 second, 200 μm spot) | SNR (1 second, 1000 μm spot) | SNR (10 second, 1000 μm spot) | SNR (10 second, 1000 μm spot) |
| Peak (1142) | 1241 (SNR >5) | 25 (SNR >5) | 1 7 (SNR <5) | 3.17 (SNR <5) | 17 (SNR >5) |
| Area (300-2000) | 4615 (SNR >5) | 92 (SNR >5) | 3.7 (SNR <5) | 11.7 (SNR >5) | 62 (SNR >5) |

An analysis of different readers was conducted by interchanging lasers, detectors, gratings, apertures, and lens in a compact test bed spectrometer was performed. This analysis resulted in gold standard systems (and/or highly cooled CCD) with cost of goods sold (COGS) of less than $1000. The primary cost drivers are the laser and detector. A system with a low-cost VCSEL laser source and a linear CCD had spectral resolution required to resolve many tags (e.g., 100 s to 1000 s of tags) provided for in various implementations.

Figure 16:
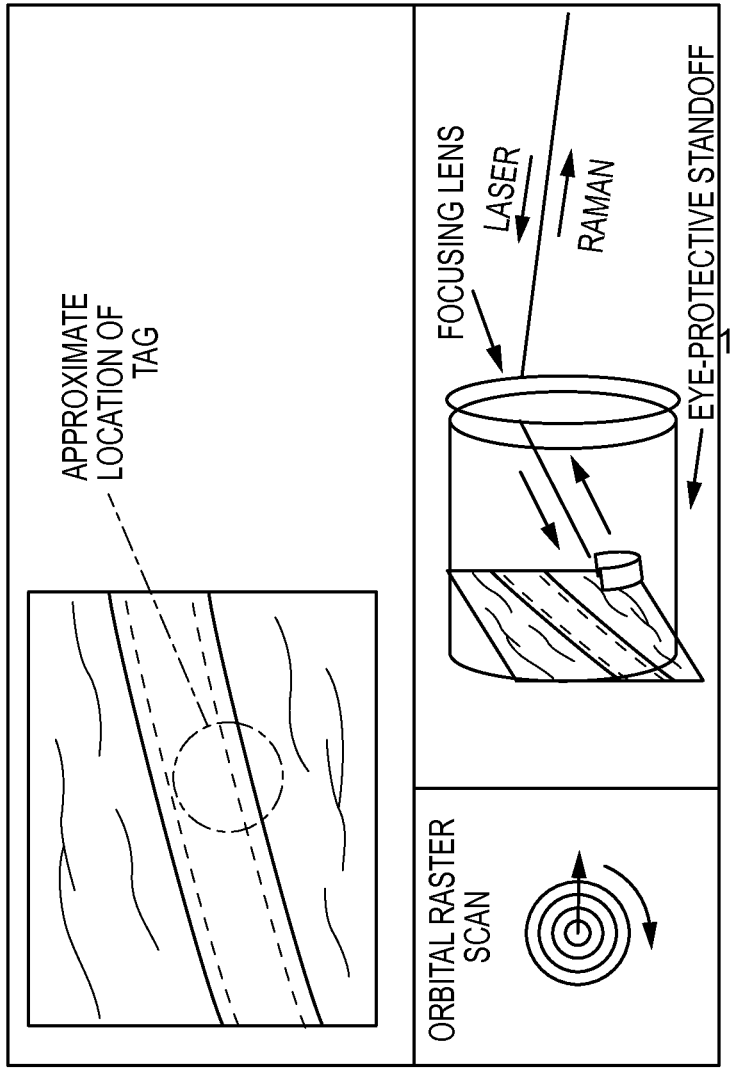
FIG. 16 shows an example implementation to detect a fiber authentication tag.

FIG. 16 illustrates one solution to this difficulty. In this solution, a reader rasters a tightly focused laser excitation beam, couples the Raman excitation from that beam to a small slit width for good spectral resolution, and maintains high spectral throughput with a low f/# collection lens and spectrograph. The orbital raster scan (ORS™) from SnRI rather than using a large spot size maintains a small instantly coupled beam size to aperture design. The net effect is an averaged spot size that allows the end user to place the device near the thread of interest and scan an area large enough to locate the thread. The difference between this design and current Raman systems is significant; we maintain a high spectral resolution and therefore Raman resolving power.

Taggant Example

Figure 17:
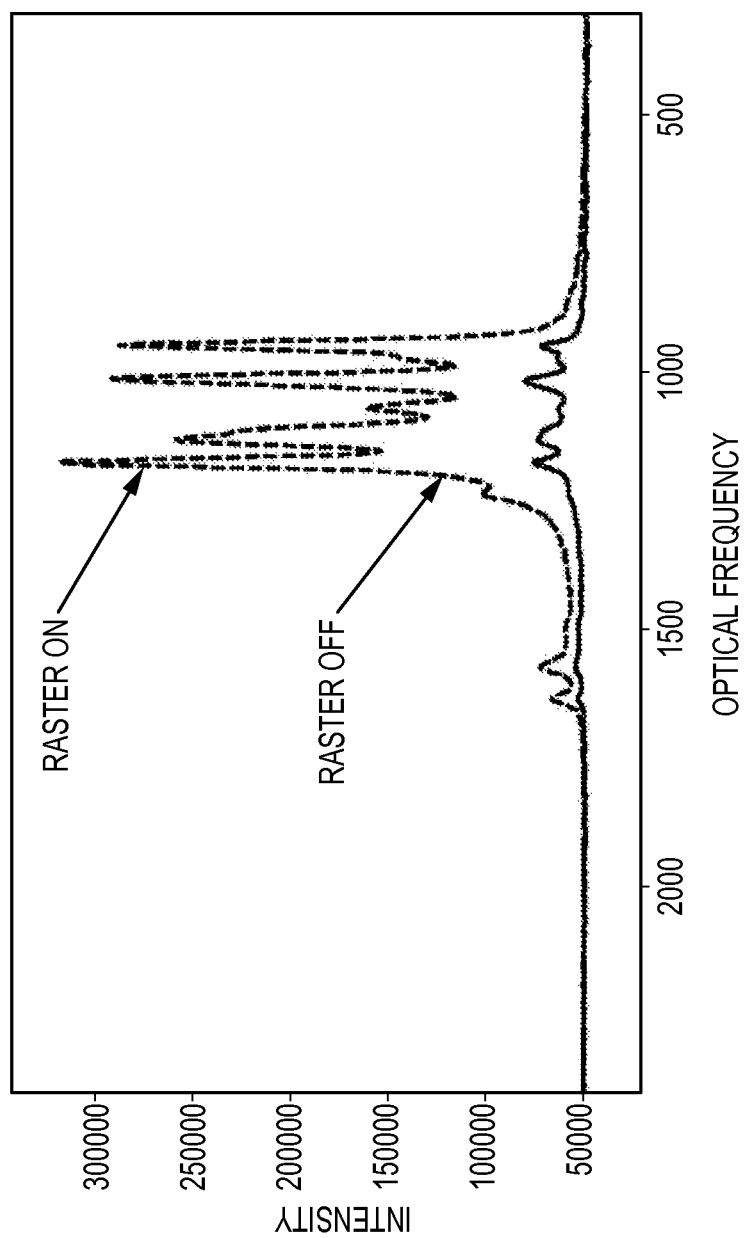
FIG. 17 shows example spectra detected with a single point focus measurement and a raster measurement.

Dispersed reporters (e.g., taggants) disposed within a sample can be detected by a spectrometer configured to move an incident beam across a surface of a sample. In one implementation, for example, panels coated with a tagged paint can be sampled by such a spectrometer. In this implementation, for example, the taggants can be at low concentrations and need not be evenly dispersed. The taggants can be luminescent materials that require high spectral resolution to resolve the spectrum. FIG. 17 shows a location with little taggant and a strong signal change at that spot due to moving a focused incident beam across the sample (e.g., rastering). FIG. 17 shows an example of a single point focus measurement (solid line) and a raster measurement (dotted line) around the same spot. The point focus is hitting a spot with little taggant. The raster scan averages an area containing large and small amounts of taggant.

Figure 18:
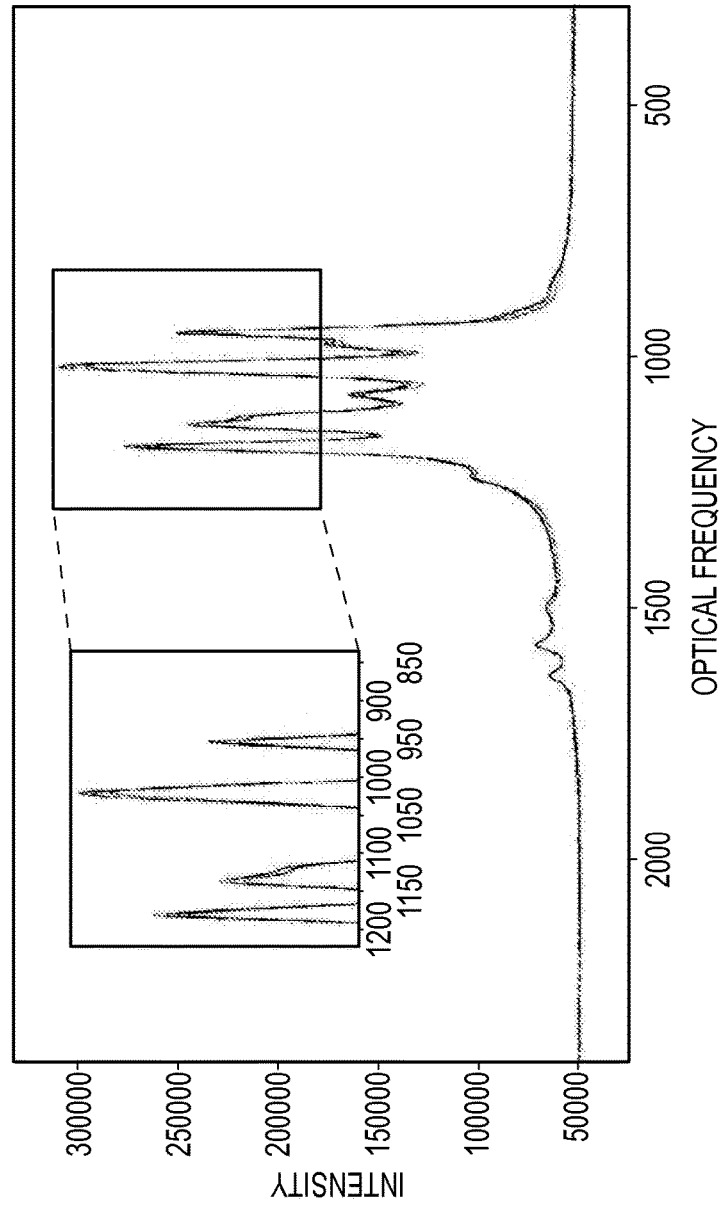
FIG. 18 shows an example illustration of averaging using a raster measurement.

FIG. 18 illustrates a small variation across a panel when moving the beam (e.g., rastering) is used. In this illustration averaging through rastering or otherwise moving an incident beam across a sample is shown. A goal of this application is to reduce the variation in the signal due to inhomogeneity of the taggants. In this particular example, rastering reduces the variation to <4%.

Figure 19:
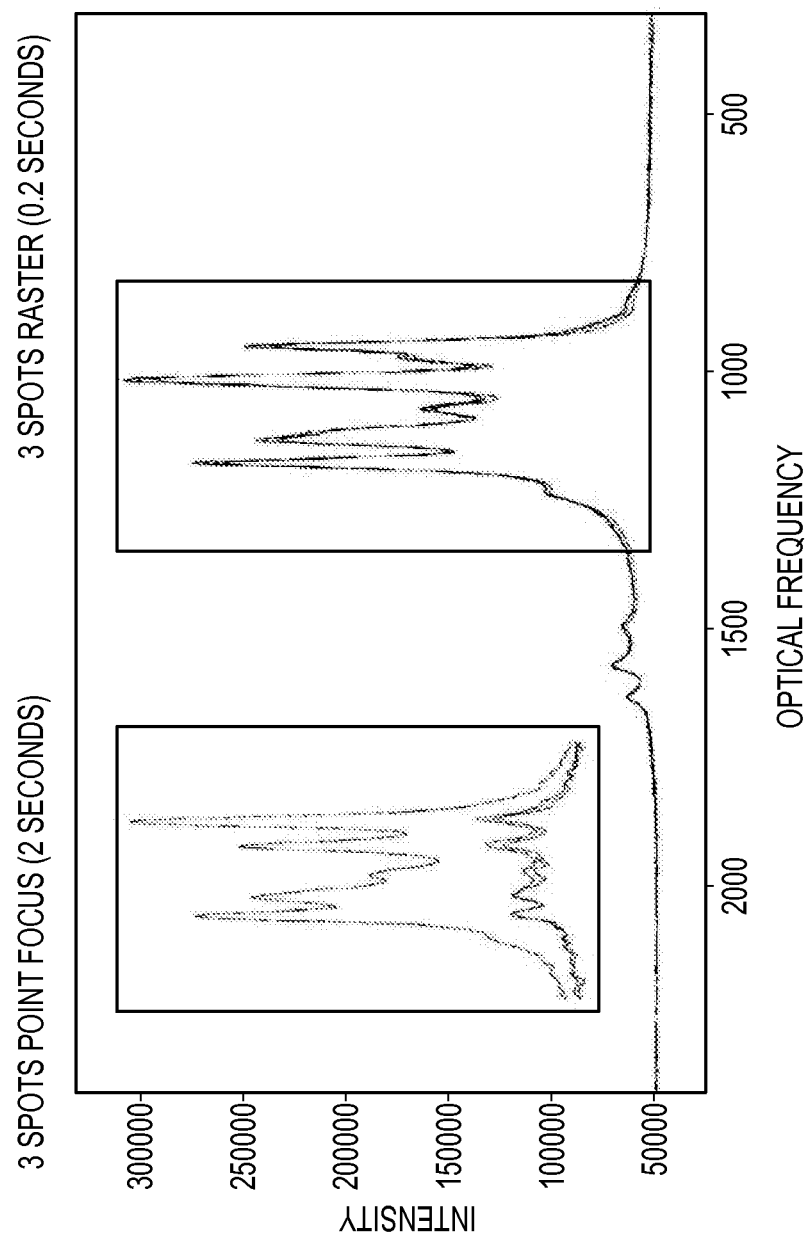
FIG. 19 shows an example illustration of single point and raster measurements for an inhomogeneous sample.

FIG. 19 illustrates the difference between an instrument which uses a point focus and an instrument with the raster scan attachment. FIG. 19 illustrates sample inhomogeneity. In this example, the left-hand box contains three measurements on a sample made with a system having a point focus. There are very large variations in the signal. The box on the right shows a rastered signals from three spots. In this example, the rastering is able to correct for an inhomogeneity.

Figure 20:
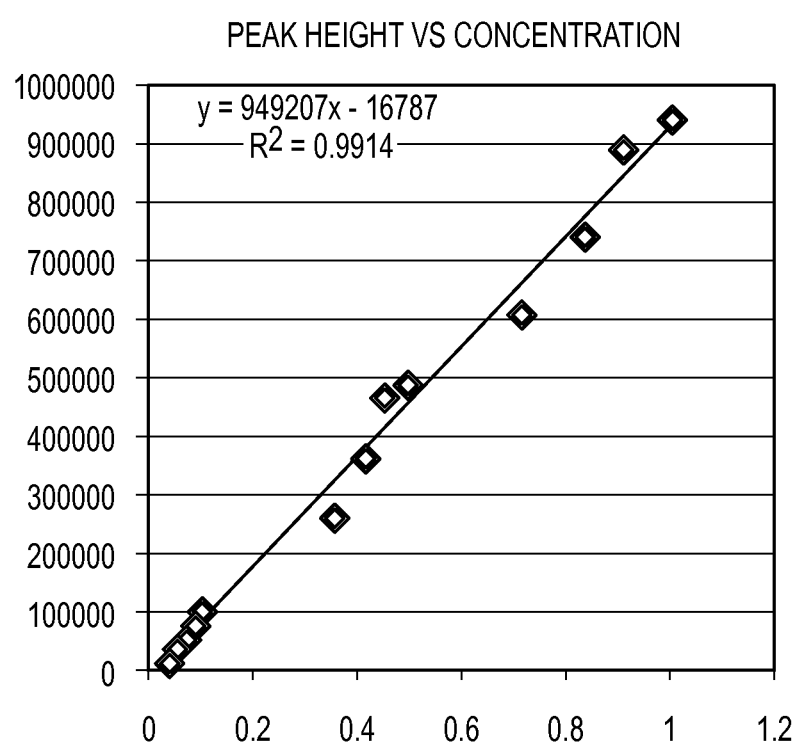
FIG. 20 shows an example illustration of removing a large variation in a measurement signal due to sample inhomogeniety.

FIG. 20 illustrates a linear regression analysis of 15 standards over a 100 fold dilution. The correlation between the raster signal and the taggant concentration is >0.99. This illustrates a goal of raster scanning in that removing the large variation in signal due to inhomogeniety allows the user to quantitate the amount of taggant in a sample. This technique can be used to validate the purity of a tagged sample.

Figure 21:
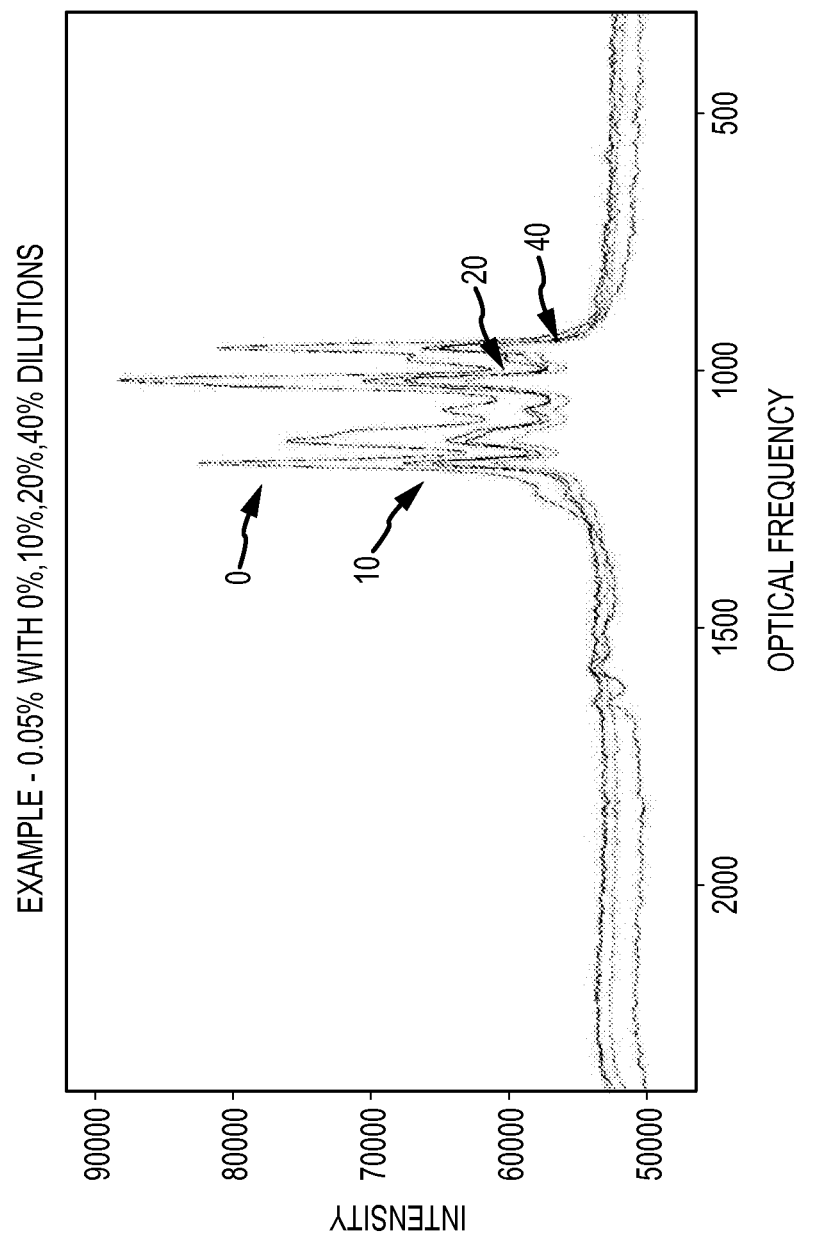
FIG. 21 shows an example illustration of observed signals on a raster scan of a sample surface as the sample is diluted.

FIG. 21 illustrates one set of painted panels with 0.05% taggants (1 part in 2000) and 4 dilutions. In this example, the intensity of the spectra correlates with the dilutions even where the taggant is highly and unevenly dispersed. This example illustrates the observed signals on a raster scan surface as the sample is diluted. In this example, the sample contains on 0.05% of the taggant and is very inhomogeneous. Raster scanning can average an area of the sample that is large enough to accurately quantitate the dilution factors.

FIG. 22 shows an example implementation of a faceted

Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A spectrometer comprising:
an excitation source for providing an excitation signal;
a detector for detecting a spectroscopy signal; and
an optical system for directing an incident beam of the excitation signal toward a sample, receiving the spectroscopy signal from the sample, and providing the spectroscopy signal to the detector, wherein the optical system comprises:
a focusing lens for focusing the incident beam from the excitation source;
a rotating mirror assembly including an angled mirror face surface; and
an actuator assembly for controlling the rotating mirror assembly to move a focused incident beam across a surface of the sample, wherein the actuator assembly comprises a rotary motor coupled to the rotating mirror assembly and adapted to rotate the angled mirror face to redirect an incident beam of the excitation signal,
wherein the rotary motor is coupled to the rotating mirror assembly via a drive shaft of the rotary motor and the rotating mirror assembly is coupled to the drive shaft of the rotary motor via a flexible mount.

2. The spectrometer of claim 1 wherein the flexible mount comprises at least one spring.

3. The spectrometer of claim 1 wherein the rotating mirror assembly is coupled loosely coupled to the drive shaft of the rotary motor configured so that the rotating mirror assembly wobbles with respect to the drive shaft when the drive shaft is turned in operation.

4. The spectrometer of claim 1 wherein the rotating mirror assembly comprises a single angled mirror surface.

5. The spectrometer of claim 1 wherein the rotating mirror assembly comprises a multi-faceted, multi-angled mirror assembly.

6. The spectrometer of claim 1 wherein the rotating mirror assembly comprises a focusing mirror.

7. The spectrometer of claim 1 wherein the spectrometer averages a plurality of signals received from the sample.

8. The spectrometer of claim 1 wherein the actuator assembly comprises a second rotary motor coupled to a second rotating mirror assembly, wherein the incident beam is directed from the rotating mirror assembly to the second rotating mirror assembly.

9. The spectrometer of claim 1 wherein a first magnet is coupled to a drive shaft of the rotary motor or the rotating mirror assembly and is adapted to align the drive shaft or the rotating mirror assembly, respectively, to a fixed position by magnetically coupling to a fixed element of the spectrometer.

10. The spectrometer of claim 9 wherein the fixed element of the spectrometer comprises a second magnet.

11. The spectrometer of claim 9 wherein the magnet comprises at least one of a permanent magnet and an electromagnet.

12. The spectrometer of claim 1 wherein a first magnet is physically coupled to the spectrometer adjacent to the actuator assembly and is adapted to magnetically couple to an element physically coupled to the drive shaft of the rotary motor or to the rotating mirror assembly and is adapted to align the mirror face surface at a predetermined position.

13. A method of moving a focused incident beam of a spectrometer across a surface of a spectroscopic sample, the method comprising:
   generating an incident beam of an excitation signal;
   directing the incident beam towards the sample via an optical system of the spectrometer;
   focusing the incident beam on a sample of the spectrometer;
   moving the incident beam across a surface of the sample by rotating a rotating mirror assembly coupled to a drive shaft of a rotary motor by rotating the drive shaft, wherein the rotating mirror assembly is coupled to the drive shaft of the rotary motor via a flexible mount;
   receiving a spectroscopic signal from the sample; and
   detecting the spectroscopic signal.

14. The method of claim 13 wherein the operation of detecting comprises averaging a plurality of spectroscopic signals received from the sample.

15. The method of claim 13 wherein rotating mirror assembly comprises a single angled mirror surface.

16. The method of claim 13 wherein the operation of detecting comprises detecting a tag at the sample.

17. The method of claim 13 wherein the operation of detecting comprises detecting a concentration of a tag at the sample.

* * * * *